(12) United States Patent
Rutter et al.

(10) Patent No.: US 9,476,881 B2
(45) Date of Patent: *Oct. 25, 2016

(54) PAS KINASE ASSAYS

(71) Applicant: University of Utah, Salt Lake City, UT (US)

(72) Inventors: Jared Paul Rutter, Salt Lake City, UT (US); Wojciech Ireneusz Swiatek, Salt Lake City, UT (US)

(73) Assignee: BioEnergenix LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/484,318

(22) Filed: Sep. 12, 2014

(65) Prior Publication Data

US 2014/0377774 A1    Dec. 25, 2014

Related U.S. Application Data

(62) Division of application No. 13/180,704, filed on Jul. 12, 2011, now Pat. No. 8,859,214.

(60) Provisional application No. 61/363,550, filed on Jul. 12, 2010.

(51) Int. Cl.
*G01N 31/00*      (2006.01)
*G01N 33/53*      (2006.01)
*G01N 33/573*     (2006.01)
*G01N 33/68*      (2006.01)

(52) U.S. Cl.
CPC ........ *G01N 33/573* (2013.01); *G01N 33/6842* (2013.01); *G01N 2333/91205* (2013.01)

(58) Field of Classification Search
CPC .......... G01N 33/573; G01N 33/6842; G01N 2333/91205
See application file for complete search history.

(56) References Cited

U.S. PATENT DOCUMENTS 6,319,679 B1 * 11/2001 McKnight ................ C12N 9/12
                                                    435/15
7,132,278 B2 * 11/2006 McKnight ................ C12N 9/12
                                                    435/194
8,859,214 B1 * 10/2014 Rutter .................. G01N 33/573
                                                    422/430

* cited by examiner

*Primary Examiner* — Lisa Cook
(74) *Attorney, Agent, or Firm* — Dennis A. Bennett; Brock Levin

(57) ABSTRACT

The present invention is directed towards methods for measuring and assaying PAS Kinase activity. The methods are useful, for example, for detecting PASK activity in a cell, and for screening for small molecule regulators of PAS kinase activity, as well as characterizing endogenous factors and stimuli that modulate PAS kinase activity, and identifying and optimizing the activity of potential PAS kinase inhibitors.

16 Claims, 7 Drawing Sheets

SEQUENCE LISTING

```
<160> NUMBER OF SEQ ID NOS: 33

<210> SEQ ID NO 1
<211> LENGTH: 498
<212> TYPE: PRT
<213> ORGANISM: Saccharomyces cerevisiae

<400> SEQUENCE: 1

Met Ser Thr Lys Lys His Thr Lys Thr His Ser Thr Tyr Ala Phe Glu
1               5                   10                  15

Ser Asn Thr Asn Ser Val Ala Ala Ser Gln Met Arg Asn Ala Leu Asn
            20                  25                  30

Lys Leu Ala Asp Ser Ser Lys Leu Asp Asp Ala Ala Arg Ala Lys Phe
        35                  40                  45
```

```
Glu Asn Glu Leu Asp Ser Phe Phe Thr Leu Phe Arg Arg Tyr Leu Val
 50                  55                  60
Glu Lys Ser Ser Arg Thr Thr Leu Glu Trp Asp Lys Ile Lys Ser Pro
 65                  70                  75                  80
Asn Pro Asp Glu Val Val Lys Tyr Glu Ile Ile Ser Gln Gln Pro Glu
                 85                  90                  95
Asn Val Ser Asn Leu Ser Lys Leu Ala Val Leu Lys Leu Asn Gly Gly
                100                 105                 110
Leu Gly Thr Ser Met Gly Cys Val Gly Pro Lys Ser Val Ile Glu Val
                115                 120                 125
Arg Glu Gly Asn Thr Phe Leu Asp Leu Ser Val Arg Gln Ile Glu Tyr
130                 135                 140
Leu Asn Arg Gln Tyr Asp Ser Asp Val Pro Leu Leu Leu Met Asn Ser
145                 150                 155                 160
Phe Asn Thr Asp Lys Asp Thr Glu His Leu Ile Lys Lys Tyr Ser Ala
                165                 170                 175
Asn Arg Ile Arg Ile Arg Ser Phe Asn Gln Ser Arg Phe Pro Arg Val
                180                 185                 190
Tyr Lys Asp Ser Leu Leu Pro Val Pro Thr Glu Tyr Asp Ser Pro Leu
                195                 200                 205
Asp Ala Trp Tyr Pro Pro Gly His Gly Asp Leu Phe Glu Ser Leu His
210                 215                 220
Val Ser Gly Glu Leu Asp Ala Leu Ile Ala Gln Gly Arg Glu Ile Leu
225                 230                 235                 240
Phe Val Ser Asn Gly Asp Asn Leu Gly Ala Thr Val Asp Leu Lys Ile
                245                 250                 255
Leu Asn His Met Ile Glu Thr Gly Ala Glu Tyr Ile Met Glu Leu Thr
                260                 265                 270
Asp Lys Thr Arg Ala Asp Val Lys Gly Gly Thr Leu Ile Ser Tyr Asp
                275                 280                 285
Gly Gln Val Arg Leu Leu Glu Val Ala Gln Val Pro Lys Glu His Ile
290                 295                 300
Asp Glu Phe Lys Asn Ile Arg Lys Phe Thr Asn Phe Asn Thr Asn Asn
305                 310                 315                 320
Leu Trp Ile Asn Leu Lys Ala Val Lys Arg Leu Ile Glu Ser Ser Asn
                325                 330                 335
Leu Glu Met Glu Ile Ile Pro Asn Gln Lys Thr Ile Thr Arg Asp Gly
                340                 345                 350
His Glu Ile Asn Val Leu Gln Leu Glu Thr Ala Cys Gly Ala Ala Ile
                355                 360                 365
Arg His Phe Asp Gly Ala His Gly Val Val Pro Arg Ser Arg Phe
370                 375                 380
Leu Pro Val Lys Thr Cys Ser Asp Leu Leu Leu Val Lys Ser Asp Leu
385                 390                 395                 400
Phe Arg Leu Glu His Gly Ser Leu Lys Leu Asp Pro Ser Arg Phe Gly
                405                 410                 415
Pro Asn Pro Leu Ile Lys Leu Gly Ser His Phe Lys Lys Val Ser Gly
                420                 425                 430
Phe Asn Ala Arg Ile Pro His Ile Pro Lys Ile Val Glu Leu Asp His
                435                 440                 445
Leu Thr Ile Thr Gly Asn Val Phe Leu Gly Lys Asp Val Thr Leu Arg
450                 455                 460
Gly Thr Val Ile Ile Val Cys Ser Asp Gly His Lys Ile Asp Ile Pro
```

```
                465                 470                 475                 480
        Asn Gly Ser Ile Leu Glu Asn Val Val Thr Gly Asn Leu Gln Ile
                        485                 490                 495

Leu Glu

<210> SEQ ID NO 2
<211> LENGTH: 1323
<212> TYPE: PRT
<213> ORGANISM: Homo sapiens

<400> SEQUENCE: 2

Met Glu Asp Gly Gly Leu Thr Ala Phe Glu Asp Gln Arg Cys Leu
 1               5                  10                  15

Ser Gln Ser Leu Pro Leu Pro Val Ser Ala Glu Gly Pro Ala Gln
                20                  25                  30

Thr Thr Ala Glu Pro Ser Arg Ser Phe Ser Ser Ala His Arg His Leu
                35                  40                  45

Ser Arg Arg Asn Gly Leu Ser Arg Leu Cys Gln Ser Arg Thr Ala Leu
 50                  55                  60

Ser Glu Asp Arg Trp Ser Ser Tyr Cys Leu Ser Ser Leu Ala Ala Gln
65                   70                  75                  80

Asn Ile Cys Thr Ser Lys Leu His Cys Pro Ala Ala Pro Glu His Thr
                85                  90                  95

Asp Pro Ser Glu Pro Arg Gly Ser Val Ser Cys Cys Ser Leu Leu Arg
                100                 105                 110

Gly Leu Ser Ser Gly Trp Ser Ser Pro Leu Leu Pro Ala Pro Val Cys
                115                 120                 125

Asn Pro Asn Lys Ala Ile Phe Thr Val Asp Ala Lys Thr Thr Glu Ile
                130                 135                 140

Leu Val Ala Asn Asp Lys Ala Cys Gly Leu Leu Gly Tyr Ser Ser Gln
145                 150                 155                 160

Asp Leu Ile Gly Gln Lys Leu Thr Gln Phe Phe Leu Arg Ser Asp Ser
                165                 170                 175

Asp Val Val Glu Ala Leu Ser Glu Glu His Met Glu Ala Asp Gly His
                180                 185                 190

Ala Ala Val Val Phe Gly Thr Val Asp Ile Ile Ser Arg Ser Gly
                195                 200                 205

Glu Lys Ile Pro Val Ser Val Trp Met Lys Arg Met Arg Gln Glu Arg
                210                 215                 220

Arg Leu Cys Cys Val Val Leu Glu Pro Val Glu Arg Val Ser Thr
225                 230                 235                 240

Trp Val Ala Phe Gln Ser Asp Gly Thr Val Thr Ser Cys Asp Ser Leu
                245                 250                 255

Phe Ala His Leu His Gly Tyr Val Ser Gly Glu Asp Val Ala Gly Gln
                260                 265                 270

His Ile Thr Asp Leu Ile Pro Ser Val Gln Leu Pro Pro Ser Gly Gln
                275                 280                 285

His Ile Pro Lys Asn Leu Lys Ile Gln Arg Ser Val Gly Arg Ala Arg
                290                 295                 300

Asp Gly Thr Thr Phe Pro Leu Ser Leu Lys Leu Lys Ser Gln Pro Ser
305                 310                 315                 320

Ser Glu Glu Ala Thr Thr Gly Glu Ala Ala Pro Val Ser Gly Tyr Arg
                325                 330                 335

Ala Ser Val Trp Val Phe Cys Thr Ile Ser Gly Leu Ile Thr Leu Leu
```

```
                340             345             350
Pro Asp Gly Thr Ile His Gly Ile Asn His Ser Phe Ala Leu Thr Leu
            355             360             365

Phe Gly Tyr Gly Lys Thr Glu Leu Leu Gly Lys Asn Ile Thr Phe Leu
            370             375             380

Ile Pro Gly Phe Tyr Ser Tyr Met Asp Leu Ala Tyr Asn Ser Ser Leu
385             390             395             400

Gln Leu Pro Asp Leu Ala Ser Cys Leu Asp Val Gly Asn Glu Ser Gly
            405             410             415

Cys Gly Glu Arg Thr Leu Asp Pro Trp Gln Gly Gln Asp Pro Ala Glu
            420             425             430

Gly Gly Gln Asp Pro Arg Ile Asn Val Val Leu Ala Gly Gly His Val
            435             440             445

Val Pro Arg Asp Glu Ile Arg Lys Leu Met Glu Ser Gln Asp Ile Phe
            450             455             460

Thr Gly Thr Gln Thr Glu Leu Ile Ala Gly Gly Gln Leu Leu Ser Cys
465             470             475             480

Leu Ser Pro Gln Pro Ala Pro Gly Val Asp Asn Val Pro Glu Gly Ser
            485             490             495

Leu Pro Val His Gly Glu Gln Ala Leu Pro Lys Asp Gln Gln Ile Thr
            500             505             510

Ala Leu Gly Arg Glu Glu Pro Val Ala Ile Glu Ser Pro Gly Gln Asp
            515             520             525

Leu Leu Gly Glu Ser Arg Ser Glu Pro Val Asp Val Lys Pro Phe Ala
            530             535             540

Ser Cys Glu Asp Ser Glu Ala Pro Val Pro Ala Glu Asp Gly Gly Ser
545             550             555             560

Asp Ala Gly Met Cys Gly Leu Cys Gln Lys Ala Gln Leu Glu Arg Met
            565             570             575

Gly Val Ser Gly Pro Ser Gly Ser Asp Leu Trp Ala Gly Ala Ala Val
            580             585             590

Ala Lys Pro Gln Ala Lys Gly Gln Leu Ala Gly Gly Ser Leu Leu Met
            595             600             605

His Cys Pro Cys Tyr Gly Ser Glu Trp Gly Leu Trp Trp Arg Ser Gln
            610             615             620

Asp Leu Ala Pro Ser Pro Ser Gly Met Ala Gly Leu Ser Phe Gly Thr
625             630             635             640

Pro Thr Leu Asp Glu Pro Trp Leu Gly Val Glu Asn Asp Arg Glu Glu
            645             650             655

Leu Gln Thr Cys Leu Ile Lys Glu Gln Leu Ser Gln Leu Ser Leu Ala
            660             665             670

Gly Ala Leu Asp Val Pro His Ala Glu Leu Val Pro Thr Glu Cys Gln
            675             680             685

Ala Val Thr Ala Pro Val Ser Ser Cys Asp Leu Gly Gly Arg Asp Leu
            690             695             700

Cys Gly Gly Cys Thr Gly Ser Ser Ala Cys Tyr Ala Leu Ala Thr
705             710             715             720

Asp Leu Pro Gly Gly Leu Glu Ala Val Glu Ala Gln Glu Val Asp Val
            725             730             735

Asn Ser Phe Ser Trp Asn Leu Lys Glu Leu Phe Phe Ser Asp Gln Thr
            740             745             750

Asp Gln Thr Ser Ser Asn Cys Ser Cys Ala Thr Ser Glu Leu Arg Glu
            755             760             765
```

```
Thr Pro Ser Ser Leu Ala Val Gly Ser Asp Pro Asp Val Gly Ser Leu
    770                 775                 780

Gln Glu Gln Gly Ser Cys Val Leu Asp Asp Arg Glu Leu Leu Leu Leu
785                 790                 795                 800

Thr Gly Thr Cys Val Asp Leu Gly Gln Gly Arg Arg Phe Arg Glu Ser
                805                 810                 815

Cys Val Gly His Asp Pro Thr Glu Pro Leu Glu Val Cys Leu Val Ser
                820                 825                 830

Ser Glu His Tyr Ala Ala Ser Asp Arg Glu Ser Pro Gly His Val Pro
        835                 840                 845

Ser Thr Leu Asp Ala Gly Pro Glu Asp Thr Cys Pro Ser Ala Glu Glu
        850                 855                 860

Pro Arg Leu Asn Val Gln Val Thr Ser Thr Pro Val Ile Val Met Arg
865                 870                 875                 880

Gly Ala Ala Gly Leu Gln Arg Glu Ile Gln Glu Gly Ala Tyr Ser Gly
                885                 890                 895

Ser Cys Tyr His Arg Asp Gly Leu Arg Leu Ser Ile Gln Phe Glu Val
                900                 905                 910

Arg Arg Val Glu Leu Gln Gly Pro Thr Pro Leu Phe Cys Cys Trp Leu
                915                 920                 925

Val Lys Asp Leu Leu His Ser Gln Arg Asp Ser Ala Ala Arg Thr Arg
930                 935                 940

Leu Phe Leu Ala Ser Leu Pro Gly Ser Thr His Ser Thr Ala Ala Glu
945                 950                 955                 960

Leu Thr Gly Pro Ser Leu Val Glu Val Leu Arg Ala Arg Pro Trp Phe
                965                 970                 975

Glu Glu Pro Pro Lys Ala Val Glu Leu Glu Gly Leu Ala Ala Cys Glu
                980                 985                 990

Gly Glu Tyr Ser Gln Lys Tyr Ser Thr Met Ser Pro Leu Gly Ser Gly
                995                 1000                1005

Ala Phe Gly Phe Val Trp Thr Ala Val Asp Lys Glu Lys Asn Lys
    1010                1015                1020

Glu Val Val Val Lys Phe Ile Lys Lys Glu Lys Val Leu Glu Asp
    1025                1030                1035

Cys Trp Ile Glu Asp Pro Lys Leu Gly Lys Val Thr Leu Glu Ile
    1040                1045                1050

Ala Ile Leu Ser Arg Val Glu His Ala Asn Ile Ile Lys Val Leu
    1055                1060                1065

Asp Ile Phe Glu Asn Gln Gly Phe Phe Gln Leu Val Met Glu Lys
    1070                1075                1080

His Gly Ser Gly Leu Asp Leu Phe Ala Phe Ile Asp Arg His Pro
    1085                1090                1095

Arg Leu Asp Glu Pro Leu Ala Ser Tyr Ile Phe Arg Gln Leu Val
    1100                1105                1110

Ser Ala Val Gly Tyr Leu Arg Leu Lys Asp Ile Ile His Arg Asp
    1115                1120                1125

Ile Lys Asp Glu Asn Ile Val Ile Ala Glu Asp Phe Thr Ile Lys
    1130                1135                1140

Leu Ile Asp Phe Gly Ser Ala Ala Tyr Leu Glu Arg Gly Lys Leu
    1145                1150                1155

Phe Tyr Thr Phe Cys Gly Thr Ile Glu Tyr Cys Ala Pro Glu Val
    1160                1165                1170
```

```
Leu Met Gly Asn Pro Tyr Arg Gly Pro Glu Leu Glu Met Trp Ser
    1175                1180                1185

Leu Gly Val Thr Leu Tyr Thr Leu Val Phe Glu Glu Asn Pro Phe
    1190                1195                1200

Cys Glu Leu Glu Thr Val Glu Ala Ala Ile His Pro Pro Tyr
    1205                1210                1215

Leu Val Ser Lys Glu Leu Met Ser Leu Val Ser Gly Leu Leu Gln
    1220                1225                1230

Pro Val Pro Glu Arg Arg Thr Thr Leu Glu Lys Leu Val Thr Asp
    1235                1240                1245

Pro Trp Val Thr Gln Pro Val Asn Leu Ala Asp Tyr Thr Trp Glu
    1250                1255                1260

Glu Val Phe Arg Val Asn Lys Pro Glu Ser Gly Val Leu Ser Ala
    1265                1270                1275

Ala Ser Leu Glu Met Gly Asn Arg Ser Leu Ser Asp Val Ala Gln
    1280                1285                1290

Ala Gln Glu Leu Cys Gly Gly Pro Val Pro Gly Glu Ala Pro Asn
    1295                1300                1305

Gly Gln Gly Cys Leu His Pro Gly Asp Pro Arg Leu Leu Thr Ser
    1310                1315                1320

<210> SEQ ID NO 3
<211> LENGTH: 15
<212> TYPE: PRT
<213> ORGANISM: Homo sapiens

<400> SEQUENCE: 3

Ser Leu Leu Arg Gly Leu Ser Ser Gly Trp Ser Ser Pro Leu Leu
1               5                   10                  15

<210> SEQ ID NO 4
<211> LENGTH: 15
<212> TYPE: PRT
<213> ORGANISM: Mouse

<400> SEQUENCE: 4

Ser Leu Leu Arg Gly Leu Ala Ser Gly Cys Ser Gly Ser Leu Leu
1               5                   10                  15

<210> SEQ ID NO 5
<211> LENGTH: 15
<212> TYPE: PRT
<213> ORGANISM: Homo sapiens

<400> SEQUENCE: 5

Thr Gly Glu Ala Ala Pro Val Ser Gly Tyr Arg Ala Ser Val Trp
1               5                   10                  15

<210> SEQ ID NO 6
<211> LENGTH: 15
<212> TYPE: PRT
<213> ORGANISM: Mouse

<400> SEQUENCE: 6

Asp Ser Glu Ala Ala Ser Glu Ser Gly Tyr Gln Ala Ser Val Trp
1               5                   10                  15

<210> SEQ ID NO 7
<211> LENGTH: 17
<212> TYPE: PRT
<213> ORGANISM: Homo sapiens
```

<400> SEQUENCE: 7

Ser Val Gly Arg Ala Arg Asp Gly Thr Thr Phe Pro Leu Ser Leu Lys
1               5                   10                  15

Leu

<210> SEQ ID NO 8
<211> LENGTH: 15
<212> TYPE: PRT
<213> ORGANISM: Homo sapiens

<400> SEQUENCE: 8

Glu Glu Pro Val Ala Ile Glu Ser Pro Gly Gln Asp Leu Leu Gly
1               5                   10                  15

<210> SEQ ID NO 9
<211> LENGTH: 15
<212> TYPE: PRT
<213> ORGANISM: Mouse

<400> SEQUENCE: 9

Glu Asp Pro Ser Ala Ala Glu Ser Tyr Arg Glu Ser Leu Leu Glu
1               5                   10                  15

<210> SEQ ID NO 10
<211> LENGTH: 15
<212> TYPE: PRT
<213> ORGANISM: Homo sapiens

<400> SEQUENCE: 10

Gly Gln Asp Leu Leu Gly Glu Ser Arg Ser Glu Pro Val Asp Val
1               5                   10                  15

<210> SEQ ID NO 11
<211> LENGTH: 15
<212> TYPE: PRT
<213> ORGANISM: Mouse

<400> SEQUENCE: 11

Arg Glu Ser Leu Leu Glu Glu Ser Lys Ser Lys Pro Val Asp Ala
1               5                   10                  15

<210> SEQ ID NO 12
<211> LENGTH: 15
<212> TYPE: PRT
<213> ORGANISM: Homo sapiens

<400> SEQUENCE: 12

Gly Leu Ser Phe Gly Thr Pro Thr Leu Asp Glu Pro Trp Leu Gly
1               5                   10                  15

<210> SEQ ID NO 13
<211> LENGTH: 15
<212> TYPE: PRT
<213> ORGANISM: Mouse

<400> SEQUENCE: 13

Cys Val Leu Leu Gly Thr Pro Thr Leu Asp Glu Pro Trp Pro Gly
1               5                   10                  15

<210> SEQ ID NO 14
<211> LENGTH: 15
<212> TYPE: PRT
<213> ORGANISM: Homo sapiens -continued

<400> SEQUENCE: 14

Glu Arg Gly Lys Leu Phe Tyr Thr Phe Cys Gly Thr Ile Glu Tyr
1               5                   10                  15

<210> SEQ ID NO 15
<211> LENGTH: 15
<212> TYPE: PRT
<213> ORGANISM: Mouse

<400> SEQUENCE: 15

Glu Arg Gly Lys Leu Phe Tyr Thr Phe Cys Gly Thr Ile Glu Tyr
1               5                   10                  15

<210> SEQ ID NO 16
<211> LENGTH: 15
<212> TYPE: PRT
<213> ORGANISM: Homo sapiens

<400> SEQUENCE: 16

Leu Phe Tyr Thr Phe Cys Gly Thr Ile Glu Tyr Cys Ala Pro Glu
1               5                   10                  15

<210> SEQ ID NO 17
<211> LENGTH: 15
<212> TYPE: PRT
<213> ORGANISM: Mouse

<400> SEQUENCE: 17

Leu Phe Tyr Thr Phe Cys Gly Thr Ile Glu Tyr Cys Ala Pro Glu
1               5                   10                  15

<210> SEQ ID NO 18
<211> LENGTH: 15
<212> TYPE: PRT
<213> ORGANISM: Homo sapiens

<400> SEQUENCE: 18

Pro Val Pro Glu Arg Arg Thr Thr Leu Glu Lys Leu Val Thr Asp
1               5                   10                  15

<210> SEQ ID NO 19
<211> LENGTH: 15
<212> TYPE: PRT
<213> ORGANISM: Mouse

<400> SEQUENCE: 19

Pro Cys Pro Glu Gln Arg Thr Thr Leu Glu Lys Leu Ile Arg Asp
1               5                   10                  15

<210> SEQ ID NO 20
<211> LENGTH: 15
<212> TYPE: PRT
<213> ORGANISM: Homo sapiens

<400> SEQUENCE: 20

Phe Arg Val Asn Lys Pro Glu Ser Gly Val Leu Ser Ala Ala Ser
1               5                   10                  15

<210> SEQ ID NO 21
<211> LENGTH: 15
<212> TYPE: PRT
<213> ORGANISM: Mouse

<400> SEQUENCE: 21

```
Cys Arg Thr Asn Gln Pro Glu Ser Gly Leu Leu Ser Ala Ala Ser
1               5                   10                  15

<210> SEQ ID NO 22
<211> LENGTH: 15
<212> TYPE: PRT
<213> ORGANISM: Homo sapiens

<400> SEQUENCE: 22

Lys Pro Glu Ser Gly Val Leu Ser Ala Ala Ser Leu Glu Met Gly
1               5                   10                  15

<210> SEQ ID NO 23
<211> LENGTH: 15
<212> TYPE: PRT
<213> ORGANISM: Mouse

<400> SEQUENCE: 23

Gln Pro Glu Ser Gly Leu Leu Ser Ala Ala Ser Leu Glu Ile Gly
1               5                   10                  15

<210> SEQ ID NO 24
<211> LENGTH: 15
<212> TYPE: PRT
<213> ORGANISM: Homo sapiens

<400> SEQUENCE: 24

Ser Gly Val Leu Ser Ala Ala Ser Leu Glu Met Gly Asn Arg Ser
1               5                   10                  15

<210> SEQ ID NO 25
<211> LENGTH: 15
<212> TYPE: PRT
<213> ORGANISM: Mouse

<400> SEQUENCE: 25

Ser Gly Leu Leu Ser Ala Ala Ser Leu Glu Ile Gly Ser Arg Ser
1               5                   10                  15

<210> SEQ ID NO 26
<211> LENGTH: 15
<212> TYPE: PRT
<213> ORGANISM: Homo sapiens

<400> SEQUENCE: 26

Glu Met Gly Asn Arg Ser Leu Ser Asp Val Ala Gln Ala Gln Glu
1               5                   10                  15

<210> SEQ ID NO 27
<211> LENGTH: 15
<212> TYPE: PRT
<213> ORGANISM: Mouse

<400> SEQUENCE: 27

Glu Ile Gly Ser Arg Ser Pro Ser Glu Met Ala Gln Arg Glu Gly
1               5                   10                  15

<210> SEQ ID NO 28
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: misc_feature
```

-continued

```
<222> LOCATION: (2)..(3)
<223> OTHER INFORMATION: Xaa can be any naturally occurring amino acid

<400> SEQUENCE: 28

Arg Xaa Xaa Ser
1

<210> SEQ ID NO 29
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(3)
<223> OTHER INFORMATION: Xaa can be any naturally occurring amino acid

<400> SEQUENCE: 29

Arg Xaa Xaa Thr
1

<210> SEQ ID NO 30
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 30

Arg Arg Xaa Ser
1

<210> SEQ ID NO 31
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 31

Arg Arg Xaa Thr
1

<210> SEQ ID NO 32
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 32

Arg Xaa Arg Xaa Xaa Ser
1               5
```

```
<210> SEQ ID NO 33
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 33

Arg Xaa Arg Xaa Xaa Thr
 1               5
```

PAS KINASE ASSAYS

CROSS REFERENCE TO RELATED APPLICATIONS

This application is a divisional application of U.S. non-provisional application Ser. No. 13/180,704, filed Jul. 12, 2011, now issued as U.S. Pat. No. 8,859,214, which claims the benefit of priority of U.S. provisional application No. 61/363,550, filed Jul. 12, 2010, the disclosures of which are incorporated by reference herein in their entireties.

BACKGROUND OF THE INVENTION

Field of the Invention

The present invention relates to methods for determining the activity of PAS kinase, and the use of such assays for high throughput screening.

Protein kinases represent a large class of enzymes that function in the catalysis of phosphoryl transfer, mediating the transfer of a phosphate group from ATP to a protein substrate. Protein kinases are responsible for the control of a wide variety of signal transduction processes within the cell, and may be categorized into families by the substrates and motifs that they recognize and phosphorylate. The Ser/Thr protein kinase family of enzymes for example, comprises more than 400 members including 6 major subfamilies (AGC, CAMK, CMGC, GYC, TKL, STE). Many of these enzymes are considered targets for pharmaceutical intervention in various disease states.

Phosphorylation of target proteins occurs in response to a variety of extracellular signals including hormones, neurotransmitters, environmental stresses, as well as cell cycle events, and environmental or nutritional changes, etc. Protein kinase catalyzed phosphorylation events can act as molecular switches to modulate or regulate the biological function, or spatiotemporal position of the target protein. Thus, protein kinases can function in signaling pathways to activate or inactivate, or modulate the activity (either directly or indirectly) of the targets. These targets may include, for example, metabolic enzymes, regulatory proteins, receptors, cytoskeletal proteins, ion channels or pumps, or transcription factors.

Consistent with their regulatory role, protein kinases play a central role in the regulation of a wide variety of cellular processes, maintaining control over cellular function. Uncontrolled signaling due to defective control of protein phosphorylation has been implicated in a number of diseases and disease conditions, including, for example, inflammation, cancer, allergy/asthma, diseases and conditions of the immune system, disease and conditions of the central nervous system (CNS), cardiovascular disease, dermatology, ocular diseases and angiogenesis. The development of selective protein kinase inhibitors that can block the disease pathologies and/or symptoms resulting from aberrant protein kinase activity has therefore become an important therapeutic objective.

PAS kinase (PASK) is a nutrient responsive protein kinase, which was first identified in humans by Rutter et al. in 2001 (Rutter et al. (2001) PNAS 98 8991-8996). PAS kinase is also alternatively referred to as DKFZp4340051; DKFZp686P2031; hPASK; KIAA0135; PAS domain containing serine/threonine kinase; PAS domain-containing serine/threonine-protein kinase; PAS-kinase; PAS-serine/threonine kinase; PASK; PASKIN; and STK37). The human version of PASK is encoded by a single gene located on chromosome 2, band q37. Analysis of genomic and cDNA clones of PASK has shown the gene to be composed of 18 coding exons covering roughly 37 kilobases of human chromosome 2. The enzyme is 1,323 amino acid residues in length and highly related in primary sequence to polypeptides specified in the genomes of flies and yeast. RT-PCR assays conducted on multiple tissues of the mouse indicate that PASK mRNA is expressed at a similar level in all tissues. (U.S. Pat. Nos. 7,132,278 & 6,319,679).

PAS kinase includes three conserved regions that include 2 "PAS" domains, and a C-terminal catalytic kinase domain. The term "PAS" is derived from the abbreviation of three PAS fold-containing transcription factors, period (PER); aryl hydrocarbon receptor nuclear translocator (ARNT); and single-minded (SIM). PAS domains usually consist of two adjacent degenerate repeats of about 130 amino acids, called PAS A and PAS B. PAS domains are typically found in environmental protein sensors involved in the perception of external signals including light intensity, gas partial pressures, redox potential and specific organic ligands. (Ponting and Aravind (1977) Curr. Biol. 7 R 674-R677; Zhulin & Taylor (1997) Trends. Biochem. Sci. 22 331-333; Taylor & Zhulin (1999) Microbiol. Mol. Biol. Rev. 63 479-506; Gu et al., (2000) Annul. Rev. Pharmacol. Toxicol. 40 519-561).

Biophysical studies of the two PAS domains of PASK have identified PAS-A as a ligand-binding regulatory domain of the PASK enzyme. The 3-diminensional structure of the PASK domain has been resolved, and synthetic ligands binding to this domain have been identified. (Amezcua et al., (2002) Structure 10 1349-1361). However these synthetic ligands bind with low affinity, and have no known cellular role. To date, no endogenous ligand for PASK has been identified. Sequence analysis of the amino acid sequence of the catalytic kinase domain of PASK reveals that it is more similar to those of the AMPK/Snf1 and Pim1 enzymes than any other proteins in public databases. PASK also exists as a nuclear phosphoprotein in HeLa cells where it is phosphorylated at Ser116 (Beausoleil, et al., (2004) PNAS 101 12130-12135; Dephoure N, et al. (2008). PNAS 105, 10762-7). Several other phosphorylation sites of PAS kinase have also identified including those at positions S333, S524, S533, T642, T1161, T1165, S1273, S1277, S1280 and S1289 (Dephoure N, et al. (2008). PNAS 105, 10762-7). However with the exception of T1161 and T1165, the functional significance of phosphorylation at these sites is unknown.

In yeast, two closely related PASK genes have been identified, PSK1 and PSK2 (Rutter et al., (2002) Cell 111 17-28)). These genes phosphorylate three translation factors and two enzymes involved in the regulation of glycogen and trehalose synthesis, suggesting that they might coordinately control translation and sugar flux. Under specific stress conditions, yeast glycogen synthase and UDP-glucose pyrophosphorylase (Ugp1) are phosphorylated by PSK1 and PSK2, resulting in the down regulation of carbohydrate storage, whereas deficiency in PSK1 and PSK2 resulted in elevated glycogen stores. (Smith & Rutter (2007) Mol. Cell. 26 491-499).

Upon phosphorylation at Serine 11 by PSK1 & 2, Ugp1 translocates to the plasma membrane where it increases cell wall glucan synthesis at the expense of glycogen storage. In the absence of PSKs, glycogen rather than glucan is produced, affecting the strength of the cell wall. (Smith & Rutter (2007) Mol. Cell. 26 491-499). Surprisingly, mammalian Ugp1 is not a human PASK target, and the yeast Ugp1 ser11 phosphorylation site is not conserved in mammalian Ugp1. (Gross et al. (2007) EMBO J. 26 4824-4830).

In mammalian cells, PASK inactivates glycogen synthase by phosphorylation at Ser640. The middle region of PASK between the PAS and kinase domains interacts with glycogen synthase. Glycogen inhibits this interaction, suggesting a glycogen-sensing function. (Hao et al., (2008) IUBMB Life 60 204-209).

Recently it has been established that mice lacking PASK activity, (PASK−/− mice) exhibit impaired glucose stimulated insulin secretion, altered triglyceride storage, and an increased metabolic rate in skeletal muscle compared to wild type mice. Additionally, PASK deletion in these mice caused nearly complete protection from the deleterious effects of a high fat diet including obesity and insulin resistance. (Hao et al., (2007) P.N.A.S. 104 (39) 15466-1547). Thus this data suggests that PASK plays an important role in changing environmental conditions—particularly those associated with nutrition, glucose and intracellular energy and redox sensing. Accordingly the pharmaceutical inhibition of PASK activity is likely to be useful for the treatment and/or prevention of metabolic syndrome, diabetes, obesity and related conditions, especially in light of the observation that PASK knockout has no apparent adverse health effects.

Indeed because of changes in diet and lifestyle, the incidence of the metabolic syndrome, obesity and type 2 diabetes is increasing dramatically worldwide. The world health organization estimates that the current decade will witness a 46% increase in diabetic incidence worldwide (from 151 million to 221 million), with the vast majority of this increase being due to metabolic syndrome-related type 2 diabetes. Thus there exists a large unmet need to develop more effective therapies to treat and prevent the development of metabolic syndromes.

Accordingly the development of small molecule compounds capable of modulating PASK activity, and thus of creating new therapeutic treatments for treating and/or preventing the development of metabolic syndromes is highly desirable. Central to meeting this need is the development of reliable assays to measure PASK activity, and in particular reliable cell based assays to measure intracellular PASK activity.

However, despite advances in the understanding of PASK activity in vitro, the complex spatiotemporal and environmental sensitivity of the regulation of PASK activity in vivo presents a barrier to accurately measuring intracellular PASK activity. Accordingly there remains a critical need for improved methods for evaluating the activity of such compounds within the context of living cells. The invention described herein provides new specific assay methods that can rapidly and quantitatively determine the level of PAS kinase activity either in vitro, or in cells, a result which has not previously been reported in the medical literature. Unlike previously reported assays, the PAS kinase assays of the instant invention can directly measure the intracellular level of PAS kinase activity by either measuring its level of phosphorylation, or by measuring its ability to phosphorylate a novel substrate protein. Moreover these assays are robust and reproducible for use in high throughput screening of compound libraries.

SUMMARY OF THE INVENTION

In one embodiment, the present invention includes a method for determining the activity of PAS kinase comprising, providing a sample to be tested for PAS kinase activity, and determining the level of phosphorylation of the PAS kinase in the sample, wherein the level of PAS kinase phosphorylation correlates with the level of PAS kinase activity.

In another embodiment, the present invention includes a method for determining the PAS kinase inhibiting properties of a compound comprising; a) contacting a sample comprising PAS kinase activity with the compound and measuring the level of phosphorylation of the PAS kinase in the sample; and b) comparing the PAS kinase phosphorylation level of the sample contacted with the compound with the phosphorylation level of PAS kinase in a control sample.

In another embodiment, the present invention includes a method for identifying an agent that modulates the activity of PAS kinase comprising, a) providing a test sample comprising PAS kinase activity, b) determining the change in phosphorylation of the PAS kinase in the test sample by contacting the sample with a test agent and comparing the PAS kinase phosphorylation level with the phosphorylation level of a PAS kinase in a control sample, and c) determining whether the test agent is an agent that modulates the activity of PAS kinase based on a change in phosphorylation state of PAS kinase in the test sample compared to the control sample, wherein the level of PAS kinase phosphorylation correlates with the level of PAS kinase activity.

In another embodiment, the present invention includes a method of screening a plurality of chemical compounds not known to inhibit PAS kinase activity to identify a compound which inhibits PAS kinase activity, which comprises; a) contacting a test sample comprising PAS kinase activity with the plurality of compounds not known to inhibit PAS kinase activity; b) determining the level of phosphorylation of the PAS kinase in the test sample; wherein the level of PAS kinase phosphorylation correlates with the level of PAS kinase activity; c) comparing the activity of PAS kinase in the test sample with that in a control sample; and d) where inhibition of PAS kinase activity by the plurality of compounds is observed, separately determining the inhibition of PAS kinase activity of each compound included in the plurality of compounds, so as to thereby identify any individual compound included therein which inhibits PAS kinase.

In another embodiment, the present invention includes a method of preparing a composition comprising a chemical compound which inhibits PAS kinase activity, which comprises identifying a chemical that inhibits the activity of PAS kinase comprising, a) providing a test sample comprising PAS kinase activity; b) contacting the test sample with a test chemical; c) determining the degree of reduction of phosphorylation of the PAS kinase in the test sample compared to a control sample to determine the degree of inhibition of activity of PAS kinase in the test sample, wherein the level of PAS kinase phosphorylation directly correlates with the level of PAS kinase activity; d) identifying the test chemical as a chemical that inhibits the activity of PAS kinase, and admixing the test chemical so identified, or a functional analog or homolog of the test chemical, with a carrier, thereby preparing the composition.

In one aspect of any of these methods, the test sample comprises mammalian cells having intracellular PAS kinase activity. In one aspect of any of these methods, the mammalian cells are transfected, or transformed with a nucleic acid encoding human PAS kinase. In another aspect of any of these methods, the PAS kinase is epitope tagged.

In one aspect of any of these methods, the test sample comprises purified PAS kinase. In one aspect of any of these methods the test sample also comprises ATP.

In one aspect of any of these methods, the level of phosphorylation of the PAS kinase is determined via measuring $^{32}$P incorporation into PAS kinase. In another aspect of any of these methods, the level of phosphorylation of PAS kinase is determined using an antibody reagent which is specific to one or more phosphorylation sites on PAS kinase. In another aspect of any of these methods, the level of phosphorylation of PAS kinase is determined by electrophoretic separation of the proteins in the sample and immunoblot analysis using an antibody reagent specific to PAS kinase. In another aspect of any of these methods, the level of phosphorylation of PAS kinase is determined using a first antibody reagent which is specific to PAS kinase and a second antibody reagent which is specific to one or more phosphorylation sites on PAS kinase.

In one aspect of any of these methods, the level of phosphorylation of the PAS kinase is determined at position S116 of human PAS kinase. In one aspect of any of these methods, the level of PAS kinase phosphorylation is determined at position T307 of human PAS kinase. In one aspect of any of these methods, the level of PAS kinase phosphorylation is determined at position S333 of human PAS kinase. In one aspect of any of these methods, the level of PAS kinase phosphorylation is determined at position S524 of human PAS kinase. In one aspect of any of these methods, the level of PAS kinase phosphorylation is determined at position S533 of human PAS kinase. In one aspect of any of these methods, the level of PAS kinase phosphorylation is determined at position T642 of human PAS kinase. In one aspect of any of these methods, the level of PAS kinase phosphorylation is determined at position T1161 of human PAS kinase. In one aspect of any of these methods, the level of PAS kinase autophosphorylation is determined at position T1165 of the human PAS kinase. In one aspect of any of these methods, the level of PAS kinase autophosphorylation is determined at position T1241 of human PAS kinase. In one aspect of any of these methods, the level of PAS kinase phosphorylation is determined at position S1273 of human PAS kinase. In one aspect of any of these methods, the level of PAS kinase phosphorylation is determined at position S1277 of human PAS kinase. In one aspect of any of these methods, the level of PAS kinase phosphorylation is determined at position S1280 of human PAS kinase. In one aspect of any of these methods, the level of PAS kinase phosphorylation is determined at position S1289 of human PAS kinase.

In one aspect of any of these methods, the antibody reagent which is specific to one or more phosphorylation sites on PAS kinase is specific for phosphoserine. In one aspect of any of these methods, the antibody reagent which is specific to one or more phosphorylation sites on PAS kinase is specific for phosphothreonine. In one aspect of any of these methods, the antibody reagent which is specific to one or more phosphorylation sites on PAS kinase is specific for an AKT phosphorylation site. In one aspect the AKT phosphorylation site comprises T307 of human PASK. In one aspect the AKT phosphorylation site comprises T1241 of human PASK. In one aspect the AKT phosphorylation site comprises T1301 of mouse PASK. In one aspect the AKT phosphorylation site comprises at least 5 contiguous amino acids from SEQ. ID. No. 7. In one aspect the AKT phosphorylation site comprises at least 5 contiguous amino acids from SEQ. ID. No. 18 or SEQ. ID. No. 19.

In another aspect, the antibody reagent is specific for an AKT phosphorylation motif. In one aspect the AKT phosphorylation motif comprises the sequence RXXS (SEQ. ID. No. 28), or RXXT (SEQ. ID. No. 29), RRXS (SEQ. ID. No. 30), RRXT (SEQ. ID. No. 31), RXRXXS (SEQ. ID. No. 32), or RXRXXT (SEQ. ID. No 33), where "X" in any of SEQ. ID. Nos 28 to 33 can be any amino acid. In one embodiment, the present invention includes a method for determining the activity of PAS kinase comprising; a) providing a sample to be tested for PAS kinase activity, and b) determining the level of phosphorylation of yeast Ugp1 in the sample, wherein the level of yeast Ugp1 phosphorylation correlates with the level of PAS kinase activity.

In another embodiment, the present invention includes a method for determining the PAS kinase inhibiting properties of a compound comprising; a) contacting a sample comprising PAS kinase activity with the compound, and determining the level of phosphorylation of yeast Ugp1 in the sample, and b) comparing the level of phosphorylation of yeast Ugp1 in the sample contacted with the compound with the phosphorylation levels of yeast Ugp1 in a control sample.

In another embodiment, the present invention includes a method for identifying an agent that modulates the activity of PAS kinase comprising; a) providing a test sample comprising PAS kinase activity; b) determining the change in phosphorylation of yeast Ugp1 in the test sample by contacting the test sample with a test agent and comparing the yeast Ugp1 phosphorylation level with the phosphorylation level of yeast Ugp1 in a control sample; and, c) determining whether the test agent is an agent that modulates the activity of PAS kinase based on a change in phosphorylation state of yeast Ugp1 in the test sample compared to the control sample, wherein the level of yeast Ugp1 phosphorylation correlates with the level of PAS kinase activity.

In another embodiment, the present invention includes a method of screening a plurality of chemical compounds not known to inhibit PAS kinase activity to identify a compound which inhibits PAS kinase activity, which comprises; a) contacting a test sample comprising PAS kinase activity with the plurality of compounds not known to inhibit PAS kinase activity; b) determining the level of phosphorylation of yeast Ugp1 in the test sample; wherein the level of yeast Ugp1 phosphorylation correlates with the level of PAS kinase activity; c) comparing the activity of PAS kinase in the test sample with that in a control sample and d) where inhibition of PAS kinase activity by the plurality of compounds is observed, separately determining the inhibition of PAS kinase activity of each compound included in the plurality of compounds, so as to thereby identify any individual compound included therein which inhibits PAS kinase.

In another embodiment, the present invention includes a method of preparing a composition comprising a chemical compound which inhibits PAS kinase activity, which comprises identifying a chemical that inhibits the activity of PAS kinase comprising; a) providing a test sample comprising PAS kinase activity; b) contacting the test sample with a test chemical; c) determining the degree of inhibition of activity of PAS kinase in the test sample compared to a control sample to determine the degree of reduction of phosphorylation of yeast Ugp1 in the test sample, wherein the level of yeast Ugp1 phosphorylation directly correlates with the level of PAS kinase activity; d) identifying the test chemical as a chemical that inhibits the activity of PAS kinase, and admixing the test chemical so identified, or a functional analog or homolog of the test chemical, with a carrier, thereby preparing the composition.

In one aspect of any of these methods, the test sample comprises mammalian cells having intracellular PAS kinase activity. In one aspect of any of these methods, the mammalian cells are transfected, or transformed with a nucleic acid encoding yeast Ugp1. In another aspect of these methods, the cells are transfected, or transformed with a nucleic acid encoding PAS kinase.

In one aspect of any of these methods, the test sample comprises purified PAS kinase. In one aspect of any of these methods the test sample also comprises ATP. In one aspect of any of these methods the test sample also comprises purified yeast Ugp1.

In one aspect of any of these methods, the level of phosphorylation of yeast Ugp1 is determined via an antibody reagent which is specific to one or more PAS kinase phosphorylation sites on yeast Ugp1. In one aspect, the antibody reagent is specific to the serine 11 phosphorylation site of Ugp1.

In another aspect of any of these methods, the level of phosphorylation of yeast Ugp1 is determined via by mass spectroscopy. In one aspect of any of these methods, the level of phosphorylation of yeast Ugp1 is determined via measuring the spatiotemporal distribution of Ugp1 in the cell. In one aspect of any of these methods, the level of phosphorylation of yeast Ugp1 is determined by electrophoretic separation of the proteins. In one aspect of these methods, the level of phosphorylation of yeast Ugp1 in the sample is determined at the Serine 11 phosphorylation site on yeast Ugp1.

In another aspect of any of these methods, the level of phosphorylation of yeast Ugp1 is determined using a sandwich ELISA assay in which a first antibody reagent is specific to yeast Ugp1 and a second antibody reagent is specific to one or more kinase phosphorylation sites on yeast Ugp1. In one aspect of this method, the second antibody reagent is specific to the PAS kinase phosphorylation site on yeast Ugp1 at serine 11.

In another aspect of any of these methods, the level of phosphorylation of yeast Ugp1 is determined by electrophoretic separation of the proteins in the sample and immunoblot analysis using an antibody reagent specific to yeast Ugp1. In one aspect of this method, the antibody reagent is specific to one or more PAS kinase phosphorylation sites on yeast Ugp1. In one aspect of this method, the antibody reagent is specific to the PAS kinase phosphorylation site on yeast Ugp1 at serine 11.

In another aspect of any of these methods, the level of phosphorylation of yeast Ugp1 is determined using an immunostaining procedure using an antibody reagent specific to yeast Ugp1. In one aspect of this method, the antibody reagent is specific to one or more PAS kinase phosphorylation sites on yeast Ugp1. In one aspect of this method, the antibody reagent is specific to the PAS kinase phosphorylation site on yeast Ugp1 at serine 11.

In one aspect of any of these methods, the mammalian cells are selected from cell culture cells derived from pancreatic beta cells, skeletal cells, liver cells, fat cells, fibroblasts, and cancer, or cancer derived cells. In another aspect, the sample of cells is, or is obtained from a tissue biopsy. In another aspect the mammalian cells are human cells.

BRIEF DESCRIPTION OF THE FIGURES

A better understanding of the features and advantages of the present invention can be obtained by reference to the following detailed description that sets forth illustrative embodiments, in which the principles of the invention are utilized, and the accompanying drawings of which:

FIG. 1A) Shows extracts from yeast cell mutants that are known to have unphosphorylated Ugp1 (lane 4) and constitutively phosphorylated Ugp1 (lane 5) Note the non-specific band running immediately below the phospho-Ugp1 band in lane 5 indicated with the arrow. B) Shows extracts from HEK293T cells that were transfected with human PASK and wild-type yeast Ugp1 (to promote phosphorylation) (lane 1), or with an Ugp1-S11A mutant to eliminate phosphorylation (lane 2), or with empty vector (lane 3). Note the non-specific band running just above the phospho-Ugp1 band in lane 1—indicated with the arrow.

DETAILED DESCRIPTION OF THE INVENTION

Definitions

Figure 1:
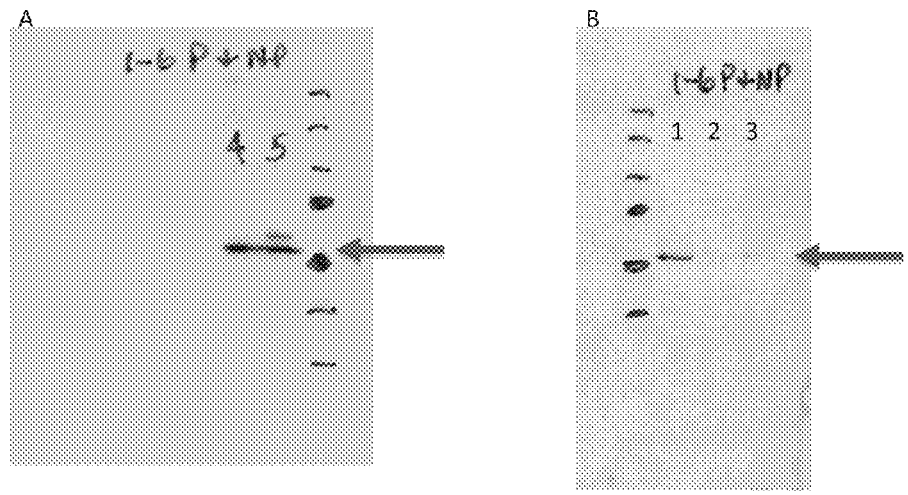
FIG. 1 Shows a western blot of cell extracts probed with an antibody specific for phosphorylated yeast Ugp1.

In order that the present disclosure may be more readily understood, certain terms are first defined. Additional definitions are set forth throughout the detailed description.

The term "about" or "approximately" means within an acceptable error range for the particular value as determined by one of ordinary skill in the art, which will depend in part on how the value is measured or determined, i.e., the limitations of the measurement system. For example, "about" can mean within 1 or 2 standard deviations, from the mean value. Alternatively, "about" with respect to the PAS kinase activity or phosphorylation state of Ugp1 can mean plus or minus a range of up to 20%, preferably up to 10%, more preferably up to 5%.

The term or "antibody" or "immunoglobulin" (used interchangeably herein) refers to a protein typically having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by beta-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains). Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments.

The term "antibody reagent" as used herein refers to an antibody preparation that can be used for the specific detection of an antigen. It can comprise individual polyclonal or monoclonal antibodies, antigen-binding fragments of these antibodies, or a cocktail of such antibodies or antibody fragments. As described in further detail herein, for quantitative detection of antigen these antibodies or antibody fragments can be labeled directly with a reporter or indirectly with a member of a specific binding pair using conventional techniques.

The terms "antigen-binding fragment", "antigen-binding domain", or "antibody fragment" are used interchangeably in the present invention to mean one or more fragments of an antibody that retain the ability to specifically bind to an antigen (see, e.g., Holliger et al., Nature Biotech. 23 (9): 1126-1129 (2005)). Non-limiting examples of antibody fragments included within, but not limited to, (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883; and Osbourn et al. (1998) Nat. Biotechnol. 16:778). Such single chain antibodies are also intended to be encompassed within the term "antigen-binding fragment" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed.

As used herein, the terms "cell," "cells," "cell line," "host cell," and "host cells," are used interchangeably and, encompass animal cells and include invertebrate, non-mammalian vertebrate and mammalian cells. All such designations include cell populations and progeny. Thus, the terms "transformants" and "transfectants" include the primary subject cell and cell lines derived therefrom without regard for the number of transfers. Exemplary non-mammalian vertebrate cells include, for example, avian cells, reptilian cells and amphibian cells. Exemplary invertebrate cells include, but are not limited to, insect cells such as, for example, caterpillar (*Spodoptera frugiperda*) cells, mosquito (*Aedes aegypti*) cells, fruitfly (*Drosophila melanogaster*) cells, Schneider cells, and *Bombyx mori* cells. See, e.g., Luckow et al., Bio/Technology 6:47-55 (1988). The cells may be differentiated, partially differentiated or undifferentiated, e.g. stem cells, including embryonic stem cells and pluripotent stem cells. Additionally tissue samples derived from organs or organ systems may be used according to the invention. Exemplary mammalian cells include, for example, cells derived from human, non-human primate, cat, dog, sheep, goat, cow, horse, pig, rabbit, rodents including mouse, hamster, rat and guinea pig and any derivatives and progenies thereof.

The terms "cell culture" or "tissue culture" refer to cells grown in suspension or grown adhered to a variety of surfaces or substrates in vessels such as roller bottles, tissue culture flasks, dishes, multi-well plates and the like.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag).

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys.

Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln.

The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gln for Asn such that a free —$NH_2$ can be maintained.

As used herein, the term "decrease" or the related terms "decreased," "reduce" or "reduced" refers to a statistically significant decrease. For the avoidance of doubt, the terms generally refer to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% or even a 100% decrease (i.e., the measured parameter is at zero).

The term "epitope tag" refers to any antigenic determinant, or any biological structure or sequence which is fused to the coding region of a protein of interest to enable the detection or purification of the protein of interest. Such fusion proteins can be identified and purified for example by using epitope tag specific antibodies. Representative examples of epitope tags include without limitation His tag (6-Histidine), HA tag (Hemagglutinin), c-Myc tag, GST tag, and V5 tags.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassays, immunoprecipitation, assaying for the biological activity of the protein, or by immunostaining of the protein followed by FACS analysis.

"Expression control sequences" are DNA regulatory sequences, such as promoters, enhancers, polyadenylation signals, terminators, internal ribosome entry sites (IRES) and the like, that provide for the expression of a coding sequence in a host cell. Exemplary expression control sequences are described in Goeddel; Gene Expression Technology: Methods in Enzymology 185, Academic Press, San Diego, Calif. (1990).

"F(ab')$_2$" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_{H\gamma 1}$ (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H 1$) of the heavy chain. Fab' fragments differ from Fab fragments by the addition of a few residues at the carboxyl terminus of the heavy chain $C_H 1$ domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., Cell, 50:667, 1987). Such proteins (and their encoding nucleic acids) have sequence homology, as reflected by their sequence similarity, whether in terms of percent identity or by the presence of specific residues or motifs and conserved positions.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control value.

The term "isolated," when used to describe PASK or Ugp1, means protein that has been identified and separated and/or recovered from a component of its natural environment. Contaminant components of its natural environment are materials that would typically interfere with research, diagnostic or therapeutic uses for the protein, and may include enzymes, hormones, and other proteinaceous or non-proteinaceous solutes. In some embodiments, the protein will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated protein will be prepared by at least one purification step.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm can also be used to determine identity.

The terms "operably linked" and "operatively linked," as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more nucleotide sequences chosen from: (a) a nucleotide sequence capable of increasing translation; (b) a nucleotide sequence capable of increasing secretion of the recombinant protein outside a cell; and (c) a nucleotide sequence capable of increasing the mRNA stability, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

The terms "polynucleotide" and "nucleic acid molecule," used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter, the rice endosperm specific glutelin (GO) promoter, CaMV35S viral promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-RE$_x$™ system (Invitrogen Carlsbad, Calif.), Lac-Switch® (Stratagene, (San Diego, Calif.) and the Cre-ER™ tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell. Methods for purification are well-known in the art. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art A purified material may contain less than about 50%, preferably less than about 75%, and most preferably less than about 90%, of the cellular components with which it was originally associated. The term "substantially pure" indicates the highest degree of purity, which can be achieved using conventional purification techniques known in the art.

The term "recombinant protein" or "recombinant polypeptide" refers to i) a protein encoded in all or part by heterologous DNA, or ii) a protein that is expressed from expression control sequences (such as a promoter, or enhancer) created in whole or part by the heterologous DNA which activates the expression of an endogenous gene. The term "heterologous DNA" refers to DNA which has been introduced into a cell that is derived from another source, or which is from the same source but is located in a different (i.e. non native) context.

A "sample" as used herein refers to a biological material which can be tested, e.g., for the presence of PAS kinase activity, or to determine if a test agent is capable of modulating the activity of PAS kinase either in vitro, or inside a cell. Such samples may contain purified or semi-purified, or non purified preparations of PAS kinase, for in vitro measurements. Samples for in vitro assays will typically also include suitable buffers and salts for maintaining the pH, and ionic strength, as well as ATP, magnesium, and appropriate phosphorylation substrates. Samples may also comprise cells comprising intracellular PAS kinase, for intracellular measurements of PAS kinase activity. Samples of cells will typically contain buffers and salts to maintain physiological ionic strength and pH and be maintained at an appropriate temperature to preserve viability. Cells may be obtained from any source, including tissue culture, or tissue samples. In one aspect, such cells are mammalian cells. A sample may also include suitable control reagents, (Control samples) as described herein.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFv molecules, see, e.g., Pluckthun in The Pharmacology of Monoclonal Antibodies, Vol. 113, Rosenburg and Moore eds. Springer-Verlag, New York, pp. 269-315 (1994).

The term "sequence similarity" refers to the degree of identity or correspondence between nucleic acid or amino acid sequences that may or may not share a common evolutionary origin (see Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Version 7, Madison, Wis.) pileup program, or using any of the programs and algorithms described above. The program may use the local homology algorithm of Smith and Waterman with the default values: Gap creation penalty=−(1+1/k), k being the gap extension number, Average match=1, Average mismatch=−0.333.

The term "specific" in the context of antibody specificity, refers to the situation in which an antibody or binding fragment shows at least a 20 fold preference in affinity, in favor of binding to its target epitope compared to any other molecules. The term is also applicable where e.g. an antigen binding domain is specific for a particular epitope which is carried by a number of antigens, in which case the antibody will be able to bind to the various antigens carrying the epitope.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "transformation" or "transfection" refers to the transfer of one or more nucleic acid molecules into a host cell or organism. Methods of introducing nucleic acid molecules into host cells include, for instance, calcium phosphate transfection, DEAE-dextran mediated transfection, microinjection, cationic lipid-mediated transfection, electroporation, scrape loading, ballistic introduction or infection with viruses or other infectious agents. "Transformed", "transduced", or "transgenic", in the context of a cell, refers to a host cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months i.e. is transiently expressed. For example, "transformed," "transformant," and "transgenic" cells have been through the transformation process and contain foreign nucleic acid. The term "untransformed" refers to cells that have not been through the transformation process.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3,4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are specifically incorporated by reference, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention.

I. Summary of the Methods of the Invention

The present invention is based in part on the applicant's discovery of robust and reliable assays for measuring the intracellular activity of PAS kinase. In one aspect these assays are based on the discovery that certain phosphorylation sites of PAS kinase correlate with the functional activity, or state of activation, of PAS kinase. In another aspect, the assays and methods of the invention are based on the applicants discovery that yeast Ugp1 is surprisingly phosphorylated in situ by a mammalian PAS kinase (PASK) when expressed in a cell having PAS kinase activity. These assays provide for the first time simple and reliable methods for determining PASK activity either in situ within a cell, or in a cell free sample.

The methods disclosed in the present application are useful, for example, for detecting PASK activity in a cell, and for screening for small molecule regulators of PAS kinase activity, endogenous factors and stimuli that modulate PAS kinase activity, and identifying and optimizing the activity of PAS kinase inhibitors. Further improvements provided by the invention are described in detail below.

In one embodiment, the present invention includes a method for determining the activity of PAS kinase comprising, providing a sample s to be tested for PAS kinase activity, and determining the level of phosphorylation of the PAS kinase in the sample, wherein the level of PAS kinase phosphorylation correlates with the level of PAS kinase activity.

In another embodiment, the present invention includes a method for determining the PAS kinase inhibiting properties of a compound comprising; a) contacting a sample comprising PAS kinase activity with the compound and measuring the level of phosphorylation of the PAS kinase of the sample; and b) comparing the PAS kinase phosphorylation levels of the sample contacted with the compound with the phosphorylation levels of PAS kinase in a control sample.

In another embodiment, the present invention includes a method for identifying an agent that modulates the activity of PAS kinase comprising, a) providing a test sample comprising PAS kinase activity; b) determining the change in phosphorylation of the PAS kinase in the test sample by contacting the sample with a test agent and comparing the PAS kinase phosphorylation level with the phosphorylation level of a PAS kinase in a control sample, and c); determining whether the test agent is an agent that modulates the activity of PAS kinase based on a change in phosphorylation state of PAS kinase in the test sample compared to the control sample, wherein the level of PAS kinase phosphorylation correlates with the level of PAS kinase activity.

In another embodiment, the present invention includes a method of screening a plurality of chemical compounds not known to inhibit PAS kinase activity to identify a compound which inhibits PAS kinase activity, which comprises; a) contacting a test sample comprising PAS kinase activity with the plurality of compounds not known to inhibit PAS kinase activity; b) determining the level of phosphorylation of the PAS kinase in the test sample; wherein the level of PAS kinase phosphorylation correlates with the level of PAS kinase activity; c) comparing the activity of PAS kinase in the test sample with that in a control sample; and d) where inhibition of PAS kinase activity by the plurality of compounds is observed, separately determining the inhibition of PAS kinase activity of each compound included in the plurality of compounds, so as to thereby identify any individual compound included therein which inhibits PAS kinase.

In another embodiment, the present invention includes a method of preparing a composition comprising a chemical compound which inhibits PAS kinase activity, which comprises identifying a chemical that inhibits the activity of PAS kinase comprising, a) providing a test sample comprising PAS kinase activity; b) contacting the test sample with a test chemical; c) determining the degree of reduction of phosphorylation of PAS kinase in the test sample compared to a control sample to determine the degree of inhibition of activity of PAS kinase in the test sample, wherein the level of PAS kinase phosphorylation directly correlates with the level of PAS kinase activity; d) identifying the test chemical as a chemical that inhibits the activity of PAS kinase, and admixing the test chemical so identified, or a functional analog or homolog of the test chemical, with a carrier, thereby preparing the composition.

In one embodiment, the present invention includes a method for determining the activity of PAS kinase comprising; a) providing a sample to be tested for PAS kinase activity, and b) determining the level of phosphorylation of yeast Ugp1 in the sample, wherein the level of yeast Ugp1 phosphorylation correlates with the level of PAS kinase activity.

In another embodiment, the present invention includes a method for identifying an agent that inhibits the activity of PAS kinase comprising; a) providing a test sample comprising PAS kinase activity; b) determining the degree of reduction of phosphorylation of yeast Ugp1 in the test sample by contacting the test sample with a test agent and comparing the yeast Ugp1 phosphorylation level with the phosphorylation level of yeast Ugp1 in a control sample; and, c) determining whether the test agent is an agent that inhibits the activity of PAS kinase based on a change in phosphorylation state of yeast Ugp1 in the test sample compared to the control sample, wherein the level of yeast Ugp1 phosphorylation correlates with the level of PAS kinase activity.

In another embodiment, the present invention includes a method of screening a plurality of chemical compounds not known to inhibit PAS kinase activity to identify a compound which inhibits PAS kinase activity, which comprises; a) contacting a test sample having PAS kinase activity with the plurality of compounds not known to inhibit PAS kinase activity; b) determining the level of phosphorylation of yeast Ugp1 in the test sample; wherein the level of yeast Ugp1 phosphorylation correlates with the level of PAS kinase activity; c) comparing the activity of PAS kinase in the test sample with that in a control sample and d) where inhibition of PAS kinase activity by the plurality of compounds is observed, separately determining the inhibition of PAS kinase activity of each compound included in the plurality of compounds, so as to thereby identify any individual compound included therein which inhibits PAS kinase.

In another embodiment, the present invention includes a method of preparing a composition comprising a chemical compound which inhibits PAS kinase activity, which comprises identifying a chemical that inhibits the activity of PAS kinase comprising; a) providing a test sample having PAS kinase activity; b) contacting the test sample with a test chemical; c) determining the degree of inhibition of activity of PAS kinase in the test sample compared to a control sample to determine the degree of reduction of phosphorylation of yeast Ugp1 in the test sample, wherein the level of yeast Ugp1 phosphorylation directly correlates with the level of PAS kinase activity; d) identifying the test chemical as a chemical that inhibits the activity of PAS kinase, and admixing the test chemical so identified, or a functional analog or homolog of the test chemical, with a carrier, thereby preparing the composition.

II. Yeast Ugp1

In any of the claimed methods the term "yeast Ugp1" refers to all naturally-occurring and synthetic forms of yeast Ugp1. In one aspect the yeast Ugp1 is obtained from a yeast selected from the genera *Hansenula, Kluyveromyces, Pichia*, Rhino-sporidium, *Saccharomyces*, and *Schizosaccharomyces*. Preferably the yeast Ugp1 is obtained from, *Saccharomyces cerivisae* or *Pichia pastoris*. Representative species and Gene bank accession numbers for various species of yeast Ugp1 are listed below in Table D1.

TABLE D1

Exemplary Ugp1 genes

| Organism | Gene Bank Accession number/Gene ID |
|---|---|
| *Saccharomyces cerevisiae* | CAA81872 |
| *Candida glabrata* | BAA93572 |
| *Candida albicans* SC5314 | XP_710250 |
| *Pichia stipitis* CBS 6054 | GeneID: 4836815 |

It will be understood that for the recombinant production of yeast Ugp1 in different mammalian species it will typically be necessary to codon optimize the nucleic acid sequence of the gene for the host organism in question. Such codon optimization can be completed by standard analysis of the preferred codon usage for the host organism in question, and the synthesis of an optimized nucleic acid via standard DNA synthesis. A number of companies provide such services on a fee for services basis and include for example, DNA2.0, (CA, USA) and Operon Technologies. (CA, USA).

The yeast Ugp1 may be in its native form, i.e., as different allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the yeast Ugp1, are also specifically included in any of the methods of the invention including for example, pyroglutamyl, iso-aspartyl, proteolytic, phosphorylated, glycosylated, reduced, oxidatized, isomerized, and deaminated variants of the yeast Ugp1.

Fragments of native or synthetic yeast Ugp1 sequences may also have the desirable functional properties of the peptide from which they derived and may be used in any of the methods of the invention. The term "fragment" as used herein thus includes fragments of yeast Ugp1 provided that the fragment retains the ability to be phosphorylated by PAS kinase to a comparable level as the whole molecule.

The term "derivative" as used herein thus refers to yeast Ugp1 sequences or fragments thereof, which have modifications as compared to the native sequence. Such modifications may be one or more amino acid deletions, additions, insertions and/or substitutions. These may be contiguous or non-contiguous. Representative variants may include those having 1 to 20, or more preferably 1 to 15, 1 to 10, or 1 to 5 amino acid substitutions, insertions, and/or deletions as compared to any of genes listed in Table D1. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); Gin (Q); Arg (R); Ser (S); Thr (T); Val (V); Trp (W); and Tyr (Y)). Any such variant or derivative of yeast Ugp1 may be used in any of the methods of the invention. Fusion proteins of yeast Ugp1 to other proteins are also included, and these fusion proteins may enhance, activity, targeting, purification, detection, stability or potency, and include for example, hexa-histidine, glutathione S-transferase (GST), and maltose binding protein (MBP) fusion proteins.

Thus, the yeast Ugp1 which may be used in any of the methods of the invention may have amino acid sequences which are substantially homologous, or substantially similar to the native yeast Ugp1 amino acid sequences, for example, to any of the native yeast Ugp1 gene sequences listed in Table D1. Alternatively, the yeast Ugp1 may have an amino acid sequence having at least 30% preferably at least 40, 50, 60, 70, 75, 80, 85, 90, 95, 98, or 99% identity with yeast Ugp1 listed in Table D1. In a one embodiment, the yeast Ugp1 for use in any of the methods of the present invention is at least 80% identical to yeast Ugp1 (SEQ. ID No. 1): Shown below, underlined and in bold in the sequence below, is a PAS kinase phosphorylation site at serine 11.

(SEQ. ID. No. 1)
```
  1 MSTKKHTKTH STYAFESNTN SVAASQMRNA LNKLADSSKL DDAARAKFEN ELDSFFTLFR

61 RYLVEKSSRT TLEWDKIKSP NPDEVVKYEI ISQQPENVSN LSKLAVLKLN GGLGTSMGCV

121 GPKSVIEVRE GNTFLDLSVR QIEYLNRQYD SDVPLLLMNS FNTDKDTEHL IKKYSANRIR

181 IRSFNQSRFP RVYKDSLLPV PTEYDSPLDA WYPPGHGDLF ESLHVSGELD ALIAQGREIL

241 FVSNGDNLGA TVDLKILNHM IETGAEYIME LTDKTRADVK GGTLISYDGQ VRLLEVAQVP

301 KEHIDEFKNI RKFTNFNTNN LWINLKAVKR LIESSNLEME IIPNQKTITR DGHEINVLQL

361 ETACGAAIRH FDGAHGVVVP RSRFLPVKTC SDLLLVKSDL FRLEHGSLKL DPSRFGPNPL

421 IKLGSHFKKV SGFNARIPHI PKIVELDHLT ITGNVFLGKD VTLRGTVIIV CSDGHKIDIP

481 NGSILENVVV TGNLQILE
```

Chemical modifications of the native yeast Ugp1 structure which retain or stabilize yeast Ugp1 activity or biological half-life may also be used with any of the methods described herein. Such chemical modification strategies include without limitation pegylation, glycosylation, and acylation (see Clark et al.: *J. Biol. Chem.* 271(36): 21969-21977, 1996; Roberts et al.: *Adv. Drug. Deliv. Rev.* 54(4): 459-476, (2002); Felix et al.: *Int. J. Pept. Protein. Res.* 46(3-4): 253-264, (1995); Garber Diabetes Obes. Metab. 7 (6) 666-74 (2005)) C- and N-terminal protecting groups and peptomimetic units may also be included.

Isomers of the native L-amino acids, e.g., D-amino acids may be incorporated in any of the above forms of yeast Ugp1, and used in any of the methods of the invention. All such variants, derivatives, fusion proteins, or fragments of Ugp1 are included, may be used in any of the methods claims or disclosed herein, and are subsumed under the term "yeast Ugp1".

In one embodiment of any of the methods of the instant invention, the sample of cells-to be tested for PAS kinase activity can be engineered to express recombinant Ugp1 protein. The recombinant Ugp1 protein may be expressed with a protein tag or as a fusion protein. In such embodiments, for the determination of the level of phosphorylated Ugp1, it is thus possible to use antibody reagents that are specific to the tag or non-Ugp1 part of such fusion proteins to substitute for antibody reagents that are specific for the native coding region of yeast Ugp1. In one aspect, the recombinant Ugp1 protein will be from *Saccharomyces cerevisiae*.

In another embodiment of any of the methods of the instant invention, the sample of cells-to be tested can be engineered to express recombinant PAS kinase.

III. PAS Kinase

The terms "PAS kinase" or "PASK" refers to all naturally-occurring and synthetic forms of PAS kinase. In one aspect, the term "PAS kinase" refers to recombinant PAS kinase. In one aspect the PAS kinase is from a vertebrate. In one aspect the PAS kinase is from a mammal. In a further embodiment the PAS kinase is human. Representative species and Gene bank accession numbers for various species of PAS kinase are listed below in Table D2.

TABLE D2

| Exemplary PAS kinase genes | |
|---|---|
| Species | Gene Bank Accession number |
| Homo sapiens | Q96RG2-1 |
| | Q96RG2-2 |

TABLE D2-continued

| Exemplary PAS kinase genes | |
|---|---|
| Species | Gene Bank Accession number |
| | Q96RG2.3 |
| | AAK69752.1 |
| Mus musculus | NM_080850 |
| | Q8CEE6 |
| Bos taurus | XP_589604.4 |
| Canis lupus familiaris | XP_851855 |
| Rattus norvegicus | NP_001009362.1 |
| | EDL91953.1 |
| | EDL91952.1 |
| Gallus gallus | XP_422656.2 |
| Danio rerio | AI544962 |

In one embodiment, the PAS kinase for use in any of the methods of the present invention is at least 80% identical to human PAS kinase (SEQ. ID No. 2) as shown below:

(SEQ. ID No. 2)

```
MEDGGLTAFE EDQRCLSQSL PLPVSAEGPA AQTTAEPSRS FSSAHRHLSR RNGLSRLCQS
RTALSEDRWS SYCLSSLAAQ NICTSKLHCP AAPEHTDPSE PRGSVSCCSL LRGLSSGWSS
PLLPAPVCNP NKAIFTVDAK TTEILVANDK ACGLLGYSSQ DLIGQKLTQF FLRSDSDVVE
ALSEEHMEAD GHAAVVFGTV VDIISRSGEK IPVSVWMKRM RQERRLCCVV VLEPVERVST
WVAFQSDGTV TSCDSLFAHL HGYVSGEDVA GQHITDLIPS VQLPPSGQHI PKNLKIQRSV
GRARDGTTFP LSLKLKSQPS SEEATTGEAA PVSGYRASVW VFCTISGLIT LLPDGTIHGI
NHSFALTLFG YGKTELLGKN ITFLIPGFYS YMDLAYNSSL QLPDLASCLD VGNESGCGER
TLDPWQGQDP AEGGQDPRIN VVLAGGHVVP RDEIRKLMES QDIFTGTQTE LIAGGQLLSC
LSPQPAPGVD NVPEGSLPVH GEQALPKDQQ ITALGREEPV AIESPGQDLL GESRSEPVDV
KPFASCEDSE APVPAEDGGS DAGMCGLCQK AQLERMGVSG PSGSDLWAGA AVAKPQAKGQ
LAGGSLLMHC PCYGSEWGLW WRSQDLAPSP SGMAGLSFGT PTLDEPWLGV ENDREELQTC
LIKEQLSQLS LAGALDVPHA ELVPTECQAV TAPVSSCDLG GRDLCGGCTG SSSACYALAT
DLPGGLEAVE AQEVDVNSFS WNLKELFFSD QTDQTSSNCS CATSELRETP SSLAVGSDPD
VGSLQEQGSC VLDDRELLLL TGTCVDLGQG RRFRESCVGH DPTEPLEVCL VSSEHYAASD
RESPGHVPST LDAGPEDTCP SAEEPRLNVQ VTSTPVIVMR GAAGLQREIQ EGAYSGSCYH
RDGLRLSIQF EVRRVELQGP TPLFCCWLVK DLLHSQRDSA ARTRLFLASL PGSTHSTAAE
LTGPSLVEVL RARPWFEEPP KAVELEGLAA CEGEYSQKYS TMSPLGSGAF GFVWTAVDKE
KNKEVVVKFI KKEKVLEDCW IEDPKLGKVT LEIAILSRVE HANIIKVLDI FENQGFFQLV
MEKHGSGLDL FAFIDRHPRL DEPLASYIFR QLVSAVGYLR LKDIIHRDIK DENIVIAEDF
TIKLIDFGSA AYLERGKLFY TFCGTIEYCA PEVLMGNPYR GPELEMWSLG VTLYTLVFEE
NPFCELEETV EAAIHPPYLV SKELMSLVSG LLQPVPERRT TLEKLVTDPW VTQPVNLADY
TWEEVFRVNK PESGVLSAAS LEMGNRSLSD VAQAQELCGG PVPGEAPNGQ GCLHPGDPRL
LTS
```

The PAS kinase may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the PAS kinase, are also specifically included in any of the methods of the invention including for example, pyroglutamyl, iso-aspartyl, proteolytic, phosphorylated, glycosylated, reduced, oxidatized, isomerized, and deaminated variants of the PAS kinase. A sample of naturally occurring variants of human PAS kinase is shown in Table D3.

TABLE D3

Natural variations in human PAS kinase

| Position | Comment/SNP Ref | Reference |
|---|---|---|
| 1111Q → QVRAGQSR in isoform 2. | Alternative sequence Q96RG2-2 | |
| 111E → K | Natural variant in a metastatic melanoma sample; somatic mutation. | Patterns of somatic mutation in human cancer genomes. "Greenman C., et al., Nature 446: 153-158(2007) |
| 2501V → I | Natural variant/ rs1470414. | Patterns of somatic mutation in human cancer genomes. "Greenman C., et al., Nature 446: 153-158(2007) |
| 4261Q → R | Natural variant rs35187712. | Patterns of somatic mutation in human cancer genomes. "Greenman C., et al., Nature 446: 153-158(2007) |
| 5121T → A | Natural variant rs56033464. | Patterns of somatic mutation in human cancer genomes. "Greenman C., et al., Nature 446: 153-158(2007) |

TABLE D3-continued

Natural variations in human PAS kinase

| Position | Comment/SNP Ref | Reference |
|---|---|---|
| 5141L → S | Natural variant rs2240543. | Patterns of somatic mutation in human cancer genomes. "Greenman C., et al., Nature 446: 153-158(2007) |
| 6841P → R | Natural variant rs56372985 | Patterns of somatic mutation in human cancer genomes. "Greenman C., et al., Nature 446: 153-158(2007) |
| 6941V → M | Natural variant rs6727226. | "Prediction of the coding sequences of unidentified human genes. IV. The coding sequences of 40 new genes (KIAA0121-KIAA0160) deduced by analysis of cDNA clones from human cell line KG-1. "Nagase T., et al., DNA Res. 2: 167-174(1995) |
| 7251G → D | Natural variant rs2005771. | Patterns of somatic mutation in human cancer genomes. "Greenman C., et al., Nature 446: 153-158(2007) |
| 7961E → K | Natural variant rs35129131. | Patterns of somatic mutation in human cancer genomes. "Greenman C., et al., Nature 446: 153-158(2007) |
| 8441P → Q | Natural variant rs36082918. | Patterns of somatic mutation in human cancer genomes. "Greenman C., et al., Nature 446: 153-158(2007) |

The PAS kinase which may be used in any of the methods of the invention may have amino acid sequences which are substantially homologous, or substantially similar to the native PAS kinase amino acid sequences, for example, to any of the native PAS kinase gene sequences listed in Tables D2 or D3. Alternatively, the PAS kinase may have an amino acid sequence having at least 30% preferably at least 40, 50, 60, 70, 75, 80, 85, 90, 95, 98, or 99% identity with the PAS kinase listed in SEQ. ID. No 2.

Fragments of native or synthetic PAS kinase sequences may also have the desirable functional properties of the peptide from which they derived and may be used in any of the methods of the invention. The term "fragment" as used herein thus includes fragments of PAS kinase provided that the fragment retains the ability to be phosphorylated by PAS kinase to a comparable level as the whole molecule. Representative fragments of PAS kinase include for example, fragments comprising the PAS1 domain (about amino acids 119 to 190), fragments comprising the PAS2 domain (about amino acids 335-402) and fragments comprising the catalytic domain (about amino acids 999 to 1251).

The term "derivative" as used herein thus refers to PAS kinase sequences or fragments thereof, which have modifications as compared to the native sequence. Such modifications may be one or more amino acid deletions, additions, insertions and/or substitutions. These may be contiguous or non-contiguous. Representative variants may include those having 1 to 20, or more preferably 1 to 15, 1 to 10, or 1 to 5 amino acid substitutions, insertions, and/or deletions as compared to any of genes listed in Tables D2 or D3. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); Gln (Q); Arg (R); Ser (S); Thr (T); Val (V); Trp (W); and Tyr (Y)). Any such variant or derivative of PAS kinase may be used in any of the methods of the invention.

Fusion proteins of PAS kinase to other proteins are also included, and these fusion proteins may enhance, activity, targeting, purification, detection, stability or potency, and include for example, epitope tags, multimerization domains, and purification tags, including without limitation for example, hexa-histidine, glutathione S-transferase (GST), and maltose binding protein (MBP) fusion proteins. It will be appreciated that a flexible molecular linker (or spacer) optionally may be interposed between, and covalently join, the PAS kinase and any of the fusion proteins disclosed herein. Any such fusion protein many be used in any of the methods or kits of the present invention.

Isomers of the native L-amino acids, e.g., D-amino acids may be incorporated in any of the above forms of PAS kinase, and used in any of the methods of the invention. All such variants, derivatives, fusion proteins, or fragments of PAS kinase are included, may be used in any of the methods claims or disclosed herein, and are subsumed under the term "PAS kinase".

In one embodiment of any of the methods of the instant invention, the sample of cells-to be tested for PAS kinase activity can be engineered to express recombinant PAS kinase protein. The recombinant PAS kinase protein may be expressed with a protein tag or as a fusion protein. In such embodiments, for the determination of the level of phosphorylated PAS kinase, it is thus possible to use antibody reagents that are specific to the tag or non-PAS kinase part of such fusion proteins to substitute for antibody reagents that are specific for the coding region of native PAS kinase. In one aspect, the recombinant PAS kinase protein will be from humans.

PAS Kinase Phosphorylation Sites

PAS kinase is known to be phosphorylated at several sites and Table D4 lists known phosphorylation sites of human and mouse PAS kinase. The level of phosphorylation of any of these positions may be determined either individually, or in any combination using the assays and methods of the present invention to assess the intracellular activity of PAS kinase.

Accordingly in another aspect of any of these methods, the level of phosphorylation of PAS kinase is determined using an antibody reagent which is specific to one or more motifs that comprise phosphorylation sites as listed in Table D4.

TABLE D4

Phosphorylation sites in human and mouse PAS Kinase

| Human | | Mouse | | |
|---|---|---|---|---|
| Amino acid modified | Motif | Amino acid modified | Motif | References |
| S116 | SLLRGLSsGWSSPLL (SEQ. ID. No. 3) | S114 | SLLRGLAsGCSGSLL (SEQ. ID. No. 4) | Dephoure N, et al. (2008). *Proc Natl Acad Sci U.S.A.* 105, 10762-7 Beausoleil SA, et al. (2004) *Proc Natl Acad Sci U.S.A.* 101, 12130-5 |
| S333 | TGEAAPVsGYRASVW (SEQ. ID. No. 5) | P331 | DSEAASEsGYQASVW (SEQ. ID. No. 6) | Dephoure N, et al. (2008) *Proc Natl Acad Sci U.S.A.* 105, 10762-7 |
| T307 | SVGRARDGtTFPLSLKL (SEQ. ID. No. 7) | N/A | | Rutter, J et al. Unpublished |
| S524 | EEPVAIEsPGQDLLG (SEQ. ID. No. 8) | S591 | EDPSAAEsYRESLLE (SEQ. ID. No. 9) | Dephoure N, et al. (2008) *Proc Natl Acad Sci U.S.A.* 105, 10762-7 |
| S533 | GQDLLGEsRSEPVDV (SEQ. ID. No. 10) | S600 | RESLLEEsKSKPVDA (SEQ. ID. No. 11) | Dephoure N, et al. (2008) *Proc Natl Acad Sci U.S.A.* 105, 10762-7 |
| T642 | GLSFGTPtLDEPWLG (SEQ. ID. No. 12) | T705 | CVLLGTPtLDEPWPG (SEQ. ID. No. 13) | Witczak CA, Fujii N, Hirshman MF, Goodyear LJ (2007) Diabetes 56, 1403-9 |
| T1161 | ERGKLFYtFCGtIEY (SEQ. ID. No. 14) | T1221 | ERGKLFYtFCGtIEY (SEQ. ID. No. 15) | Rutter J, et al. (2001) *Proc Natl Acad Sci U.S.A.* 98, 8991-6 |
| T1165 | LFYtFCGtIEYCAPE (SEQ. ID. No. 16) | T1225 | LFYtFCGtIEYCAPE (SEQ. ID. No. 17) | Rutter J, et al. (2001) *Proc Natl Acad Sci U.S.A.* 98, 8991-6 |
| T1241 | PVPERRTtLEKLVTD (SEQ. ID. No. 18) | T1301 | PCPEQRTtLEKLIRD (SEQ. ID. No. 19) | Rutter, J et al. Unpublished |
| S1273 | FRVNKPEsGVLsAAs (SEQ. ID. No. 20) | S1333 | CRTNQPEsGLLsAAs (SEQ. ID. No. 21) | Dephoure N, et al. (2008) *Proc Natl Acad Sci U.S.A.* 105, 10762-7 |
| S1277 | KPEsGVLsAAsLEMG (SEQ. ID. No. 22) | S1337 | QPEsGLLsAAsLEIG (SEQ. ID. No. 23) | Dephoure N, et al. (2008) *Proc Natl Acad Sci U.S.A.* 105, 10762-7 |
| S1280 | sGVLsAAsLEMGNRS (SEQ. ID. No. 24) | S1340 | sGLLsAAsLEIGSRS (SEQ. ID. No. 25) | Dephoure N, et al. (2008) *Proc Natl Acad Sci U.S.A.* 105, 10762-7 |
| S1289 | EMGNRSLsDVAQAQE (SEQ. ID. No. 26) | S1349 | EIGSRSPsEMAQREG (SEQ. ID. No. 27) | Dephoure N, et al. (2008) *Proc Natl Acad Sci U.S.A.* 105, 10762-7 |

In Table D4, the site(s) of phosphorylation are shown within the motif in lower case and underlined.

Accordingly in one aspect of any of the claimed methods, the antibody reagent is specific for a motif selected from SEQ. ID No. 3, SEQ. ID No. 4, SEQ. ID No. 5, SEQ. ID No. 6, SEQ. ID No. 7, SEQ. ID No. 8, SEQ. ID No. 9, SEQ. ID No. 10, SEQ. ID No. 11, SEQ. ID No. 12, SEQ. ID No. 13, SEQ. ID No. 14, SEQ. ID No. 15, SEQ. ID No. 16, SEQ. ID No. 17, SEQ. ID No. 18, SEQ. ID No. 19, SEQ. ID No. 20, SEQ. ID No. 21, SEQ. ID No. 22, SEQ. ID No. 23, SEQ. ID No. 24, SEQ. ID No. 25, SEQ. ID No. 26, and SEQ. ID No. 27.

In another aspect, of any of the claimed methods, the antibody reagent is specific for SEQ. ID. No. 3. In another aspect, the antibody reagent is specific for SEQ. ID. No. 4. In another aspect, the antibody reagent is specific for SEQ. ID. No. 5. In another aspect, the antibody reagent is specific for SEQ. ID. No. 6. In another aspect, the antibody reagent is specific for SEQ. ID. No. 7. In another aspect, the antibody reagent is specific for SEQ. ID. No. 8. In another aspect, the antibody reagent is specific for SEQ. ID. No. 9. In another aspect, the antibody reagent is specific for SEQ. ID. No. 10. In another aspect, the antibody reagent is specific for SEQ. ID. No. 11. In another aspect, the antibody reagent is specific for SEQ. ID. No. 12. In another aspect, the antibody reagent is specific for SEQ. ID. No. 13. In another aspect, the antibody reagent is specific for SEQ. ID. No. 14. In another aspect, the antibody reagent is specific for SEQ. ID. No. 15. In another aspect, the antibody reagent is specific for SEQ. ID. No. 16. In another aspect, the antibody reagent is specific for SEQ. ID. No. 17. In another aspect, the antibody reagent is specific for SEQ. ID. No. 18. In another aspect, the antibody reagent is specific for SEQ. ID. No. 19. In another aspect, the antibody reagent is specific for SEQ. ID. No. 20. In another aspect, the antibody reagent is specific for SEQ. ID. No. 21. In another aspect, the antibody reagent is specific for SEQ. ID. No. 22. In another aspect, the antibody reagent is specific for SEQ. ID. No. 23. In another aspect, the antibody reagent is specific for SEQ. ID. No. 24. In another aspect, the antibody reagent is specific for SEQ. ID. No. 25. In another aspect, the antibody reagent is specific for SEQ. ID. No. 26. In another aspect, the antibody reagent is specific for SEQ. ID. No. 27.

In another aspect, the antibody reagent is specific for an AKT phosphorylation motif. In one aspect the AKT phosphorylation motif comprises the sequence RXXS (SEQ. ID. No. 28), or RXXT (SEQ. ID. No. 29), RRXS (SEQ. ID. No. 30), or RRXT (SEQ. ID. No. 31), and RXRXXS (SEQ. ID. No. 32), or RXRXXT (SEQ. ID. No 33), where "X" in any of SEQ. ID. Nos 28 to 33 can be any amino acid.

For detecting PAS kinase activity, host cells can be genetically engineered to incorporate nucleic acids encoding PASK or the yeast Ugp1. Typically the nucleic acid will be codon optimized for high level expression in human or mammalian cells, and incorporated into an expression vector to enable the expression of the yeast Ugp1 and/or PASK in the host cell. Vectors can exist as circular, double stranded DNA, and range in size form a few kilobases (kb) to hundreds of kb. In some cases cloning vectors have been modified from naturally occurring plasmids to facilitate the cloning and recombinant manipulation of polynucleotide sequences. Many such vectors are well known in the art and commercially available; see for example, by Sambrook (In. "Molecular Cloning: A Laboratory Manual," second edition, edited by Sambrook, Fritsch, & Maniatis, Cold Spring Harbor Laboratory, (1989)), Maniatis, In: Cell Biology: A Comprehensive Treatise, Vol. 3, Gene Sequence Expression, Academic Press, NY, pp. 563-608(1980).

Expression vectors include plasmids, episomes, cosmids retroviruses or phages; and expression vector can be used to express a DNA sequence encoding yeast Ugp1 and/or PASK. The choice of promoter and other regulatory elements for such expression vectors can vary according to the intended host cell, and many such elements are available commercially, and can be readily assembled from isolated components such as the Gateway system from Invitrogen, (CA, USA). Expression systems for yeast Ugp1 and PASK can be stable or transient expression systems.

In one aspect of any of these methods, yeast Ugp1 expression can be inducible, or alternatively in another aspect, yeast Ugp1 expression can be constitutive. Inducible expression systems for yeast Ugp1 can be included in an expression vector for PASK, or can be included in a separate expression system or vector.

In one aspect of any of these methods, PASK expression can be inducible, or alternatively in another aspect, PASK expression can be constitutive. Inducible expression systems for the PASK can be included in the expression vector for the yeast Ugp1, or can be included in a separate expression system or vector.

Representative commercially available viral expression vectors include, but are not limited to, the adenovirus-based systems, such as the Per.C6 system available from Crucell, Inc., and lentiviral-based systems such as pLP1 from Invitrogen.

An episomal expression vector is able to replicate in the host cell, and persists as an extrachromosomal episome within the host cell in the presence of appropriate selective pressure. (See for example, Conese et al., Gene Therapy 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP), specific examples include the vectors pREP4, pCEP4, pREP7 from Invitrogen. The host range of EBV based vectors can be increased to virtually any eukaryotic cell type through the co-expression of EBNA1 binding protein 2 (EPB2) (Kapoor et al., EMBO. J. 20: 222-230 (2001)), vectors pcDNA3.1 from Invitrogen, and pBK-CMV from Stratagene represent non-limiting examples of an episomal vector that uses T-antigen and the SV40 origin of replication in lieu of EBNA1 and oriP.

An integrating expression vector can randomly integrate into the host cell's DNA, or can include a recombination site to enable the specific recombination between the expression vector and the host cells chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (e.g., pcDNA™5/FRT), or the cre-lox system, such as can be found in the pExchange-6 Core Vectors from Stratagene. Examples of vectors that integrate into host cell chromosomes in a random fashion include, for example, pcDNA3.1 (when introduced in the absence of T-antigen) from Invitrogen, pCI or pFN10A (ACT) Flexi® from Promega.

Alternatively, the expression vector can be used to introduce and integrate a strong promoter or enhancer sequences into a locus in the cell so as to modulate the expression of an endogenous gene of interest such as PASK (Capecchi M R. Nat Rev Genet. (2005); 6 (6):507-12; Schindehutte et al., Stem Cells (2005); 23 (1):10-5). This approach can also be used to insert an inducible promoter, such as the Tet-On promoter (U.S. Pat. Nos. 5,464,758 and 5,814,618), in to the genomic DNA of the cell so as to provide inducible expression of an endogenous gene of interest, such as PASK. The activating construct can also include targeting sequence(s) to enable homologous or non-homologous recombination of the activating sequence into a desired locus specific for the gene of interest (see for example, Garcia-Otin & Guillou, Front Biosci. (2006) 11:1108-36). Alternatively, an inducible recombinase system, such as the Cre-ER system, can be used to activate a transgene in the presence of 4-hydroxytamoxifen (Indra et al. Nuc. Acid. Res. (1999) 27 (22): 4324-4327; Nuc. Acid. Res. (2000) 28(23): e99; and U.S. Pat. No. 7,112,715).

Polynucleotides may be introduced into host cells by methods described in many standard laboratory manuals, such as Davis et al., Basic Methods in Molecular Biology (1986) and Sambrook et al., (In. "Molecular Cloning: A Laboratory Manual," second edition, edited by Sambrook, Fritsch, & Maniatis, Cold Spring Harbor Laboratory, (1989)), Maniatis, In: Cell Biology: A Comprehensive Treatise, Vol. 3, Gene Sequence Expression, Academic Press, NY, pp. 563-608(1980). Exemplary methods of introducing polynucleotides into host cells include, for instance, calcium phosphate transfection, DEAE-dextran mediated transfection, transfection, microinjection, cationic lipid-mediated transfection, electroporation, transduction, scrape loading, ballistic introduction or infection. Many of these systems are commercially available as kits.

IV. Methods for Determining the Level of PASK or Ugp1 Phosphorylation

In the practice of any of the claimed methods any of the commonly used immunoassay techniques may be used for isolation of PASK or yeast Ugp1 protein, or quantification of the phosphorylation of the proteins, including radioisotope incorporation ($^{32}P$ or $^{33}P$), immunoprecipitation, immunopurification, mass spectral analysis, immunoblotting (Western blotting), immunostaining of cultured cells or tissue sections (e.g. immunofluorescence, immunohistochemistry), genetically encoded fluorescent sensors (Kunkel et al., J. Biol. Chem. (2005) 280 (7) 5581-5587) and ELISA assays.

In one embodiment, an ELISA assay is used in which the PASK or yeast Ugp1 protein is initially captured using an anti-PASK or yeast Ugp1 antibody, and phosphorylation then assessed in a second step using a labeled anti-phospho-specific antibody.

In another embodiment, an anti-PASK or yeast Ugp1 antibody is used for isolation of the PASK or yeast Ugp1 protein, for example by immunoprecipitation, and quantification of the phosphorylation of PASK or yeast Ugp1 protein is assessed using a labeled anti-phospho antibody.

In another embodiment, PASK or yeast Ugp1 is separated from other proteins by gel electrophoresis, the separated proteins blotted onto a membrane (e.g. nitrocellulose), and a labeled anti-phospho-antibody is used to assess the level of phosphorylation of PASK or Ugp1.

Due to their speed and simplicity, such ELISA methods are particularly advantageous where a rapid assay of PAS kinase activity is required, or where large numbers of sample have to be analyzed, e.g. in a high-throughput compound screen. ELISA methods are well known to those of skill in the art, e.g. see International Patent Publication No. WO 95/14930, or Using Antibodies, A Laboratory Manual, edited by Harlow, E. and Lane, D., 1999, Cold Spring Harbor Laboratory Press, (e.g. ISBN 0-87969-544-7).

In alternate embodiments of the instant invention, other standard immunoassay formats may be used in place of the sandwich ELISA assay format for the determination of the level of phosphorylated PASK or yeast Ugp1 e.g. an antigen competition assay with phosphorylated PASK or yeast Ugp1 adsorbed onto a solid phase (e.g. a 96-well plate), with the amount of phosphorylated PASK or yeast Ugp1 in the sample being quantitated by its competition with the solid phase bound PASK or yeast Ugp1 for binding to a labeled phosphorylation-site-specific antibody in solution.

In one immunoassay format for practicing this invention, a forward sandwich assay is used in which the capture reagent (e.g. anti-PASK or anti-yeast Ugp1 antibody) has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

In another aspect of any of the claimed methods, the level of phosphorylation of PASK is determined using an immunostaining procedure with an antibody reagent that is specific to one or more phosphorylation sites on PASK. In one example of this embodiment, the antibody reagent is specific to the phosphorylation site at position S116 of the PAS kinase. In another aspect the antibody reagent is specific to the phosphorylation site at position T307 of the PAS kinase. In another aspect the antibody reagent is specific to the phosphorylation site at position S333 of the PAS kinase. In another aspect the antibody reagent is specific to the phosphorylation site at position S524 of the PAS kinase. In another aspect the antibody reagent is specific to the phosphorylation site at position S533 of the PAS kinase. In another aspect the antibody reagent is specific to the phosphorylation site at position T642 of the PAS kinase. In another aspect the antibody reagent is specific to the phosphorylation site at position T1161 of the PAS kinase. In another aspect the antibody reagent is specific to the phosphorylation site at position T1165 of the PAS kinase. In another aspect the antibody reagent is specific to the phosphorylation site at position T1241 of the PAS kinase. In another aspect the antibody reagent is specific to the phosphorylation site at position S1273 of the PAS kinase. In another aspect the antibody reagent is specific to the phosphorylation site at position S1277 of the PAS kinase. In another aspect the antibody reagent is specific to the phosphorylation site at position S1280 of the PAS kinase. In another aspect the antibody reagent is specific to the phosphorylation site at position S1289 of the PAS kinase.

In another aspect the antibody reagent is specific to one or more AKT phosphorylation sites of PASK. In one aspect the AKT phosphorylation site recognized by the antibody reagent comprises SEQ. ID. No 7. In one aspect the AKT phosphorylation site recognized by the antibody reagent comprises SEQ. ID. No 18 or SEQ. ID. No. 19.

In one aspect the AKT phosphorylation site recognized by the antibody comprises T1241 of human PASK or T1301 of mouse PASK. In one aspect the AKT phosphorylation site recognized by the antibody comprises T307 of human PASK.

In another aspect of any of the claimed methods, the level of phosphorylation of yeast Ugp1 is determined using an immunostaining procedure with an antibody reagent that is specific to one or more PAS kinase phosphorylation sites on yeast Ugp1. In one example of this embodiment, the antibody reagent is specific to the PAS kinase phosphorylation site on yeast Ugp1 at serine 11.

In another aspect of any of the claimed methods immunostaining is used to detect phosphorylated PASK or yeast Ugp1, using for example cultured cells in a flask or plate, or cell smears from tissue samples, biopsies or needle aspirates. In one aspect, the immunostaining procedure is immunohistochemical detection of phosphorylated PASK or yeast Ugp1, using for example cell smears from tissue samples, biopsies or needle aspirates, or tissue sections that have been fixed to preserve the tissue structure, e.g. by freezing, or by paraformaldehyde fixation and paraffin embedding. Standard methods for cell or tissue fixation, binding of antibody reagents, and labeling or staining can be employed in these immunostaining procedures (e.g. see Using Antibodies, A Laboratory Manual, edited by Harlow, E. and Lane, D., 1999, Cold Spring Harbor Laboratory Press (e.g. ISBN 0-87969-544-7), particularly chapters 5 and 6 on staining cells and tissues).

In another aspect of any of the claimed methods, a dot blot assay may be used for the determination of the level of phosphorylated PASK or yeast Ugp1. Accordingly, the latter embodiment provides a method for determining the intracellular activity of PASK kinase comprising, providing a sample of cells to be tested for PAS kinase activity, determining the level of phosphorylation of PASK or yeast Ugp1 in the sample by solubilizing the PASK or yeast Ugp1 protein in the cell sample, adsorbing the PASK or yeast Ugp1 protein onto a membrane (e.g. a hydrophobic membrane, nitrocellulose, nylon), and contacting with a labeled antibody reagent that is specific to one or more PAS kinase phosphorylation sites on yeast Ugp1 or to phosphorylated PASK.

In another aspect of any of the claimed methods, the phosphorylation of PASK or yeast Ugp1 is determined by the incorporation of radiolabelled isotopes (e.g. $^{32}P$ or $^{33}P$) into the phosphorylated PASK or yeast Ugp1 after appropriate incorporation of the isotope into the cell and cellular ATP pool. Alternatively, in another embodiment, phosphorylated PASK or yeast Ugp1 can be monitored by immunoassay techniques as described above but using anti-phosphoserine or anti-phosphothreonine specific antibodies as a means of determining the level of phosphorylation of PASK or yeast Ugp1, rather than antibodies specific to the different phosphorylation sites.

In another embodiment of any of the methods of the invention, the level of phosphorylation of PASK or yeast Ugp1 can be determined by electrophoretic separation of the proteins in the sample and immunoblot analysis using an antibody reagent specific to one or more PAS kinase phosphorylation sites on yeast Ugp1 or PASK. In one example of this embodiment for PASK the antibody reagent is specific to the AKT phosphorylation site on PASK. In one example of this embodiment for Ugp1, the antibody reagent is specific to the PAS kinase phosphorylation site on yeast Ugp1 at Serine 11.

In another embodiment of any of the methods of the invention, the level of phosphorylation of yeast Ugp1 or PASK can be determined by mass spectroscopy analysis. In recent years, mass spectrometry (MS) has become an increasingly viable alternative to more traditional methods of phosphorylation analysis. Typically such systems rely upon proteolytic digestion and incorporate a purification step to selectively enrich the phosphoproteins followed by tandem liquid chromatography (LC) and Mass Spectroscopy (MS) analysis of the isolated phosphopeptides.

The most widely used method for selectively enriching phosphopeptides from mixtures is immobilized metal affinity chromatography (IMAC). In this technique, metal ions, usually $Fe^{3+}$ or $Ga^{3+}$, or resins containing titanium dioxide ($TiO_2$) or other metal oxides such as zirconium dioxide are bound to a chelating support. Phosphopeptides are selectively bound because of the affinity of the metal ions for the phosphate moiety. The phosphopeptides can be released using high pH or phosphate buffer, the latter usually requiring a further desalting step before MS analysis. Limitations of this approach include possible loss of phosphopeptides due to their inability to bind to the IMAC column, difficulty in the elution of some multiply-phosphorylated peptides, and background from unphosphorylated peptides (typically acidic in nature) which also have some affinity for immobilized metal ions.

Alternatively the use of affinity columns comprising phosphospecific antibodies or ankyrin repeat proteins has been reported to enable the isolation of phosphopeptides with a specific phosphorylation motif or a general class of phosphopeptides such as phosphotyrosine containing peptides (see Tao W A, et al. Nat Methods. (2005) 2(8):591-8).

Additionally several studies have examined off-line MS analysis of IMAC-separated peptides via chemical modification and selective coupling of phosphoproteins. (See for example, Oda et al. (2001) Nat Biotechnol. 19:379-82, & Zhou et al. (Nat Biotechnol (2001) 19:375-378)).

WO2004/108948, WO2003058206, US 20030153007 & US20040161795 provides systems, software, methods and kits for detecting and/or quantifying phosphorylated polypeptides and/or acetylated polypeptides in complex mixtures, such as a lysate of a cell or cellular compartment (e.g., such as an organelle).

Many suitable mass spectrometers and protocols are readily available and suitable for use in the present invention, and include for example mass spectrometers relying on electrospray ion sources, atmospheric pressure ionization sources, and matrix assisted laser desorption ion (MALDI) sources. In certain aspects, the methods of the present invention use laser desorption ionization MS techniques. These techniques include, but are not limited to, MALDI, IR-MALDI, UV-MALDI, liquid-MALDI, surface-enhanced LDI (SELDI), surface enhanced neat desorption (SEND), desorption/ionization of silicon (DIOS), laser desorption/ laser ionization MS, laser desorption/two-step laser ionization MS, and the like. (See generally, Annan, et al. (2001) Anal. Chem. 73, 393-404; Michel, et al. (1988). J Biol. Chem. 263, 1123-1130; Nuwaysir, L. & Stults, J. (1993). J Amer. Soc. Mass Spectrom. 4, 662-669; Eng, et al. (1994). J. Amer. Soc. Mass Spectrom, 5, 976-989; Amankwa, et al. (1995). Prot. Sci. 4, 113-125; Martin, et al. (2000). Anal Chem 72, 4266 4274). Those of skill in the art will know of other ionization techniques as well as other mass spectrometric techniques useful in the present methods.

V. Antibody Reagents

In any of the claimed methods, determination of the level of phosphorylation of yeast Ugp1 or PASK may be achieved by immunoassay of the phosphorylated form(s) of yeast Ugp1 or PASK, using polyclonal or monoclonal antibodies. Antigen binding fragments of these antibodies or a cocktail of antibodies can also be used to practice the invention. These antibodies can be labeled directly with a reporter or indirectly with a member of a specific binding pair using conventional techniques. Many commercially available antibodies and phospho-specific antibody reagents are readily available and suitable for use in the present invention. Antibody reagents are also readily prepared using routine procedures known in the art, and as described herein.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., Nature 256:495 (1975), or can be made by recombinant DNA methods (see, e.g., U.S. Pat. No. 4,816,567). In certain embodiments, the "monoclonal antibodies" can also be isolated from phage antibody libraries using the techniques described in Clackson et al., Nature 352:624-628 (1991) and Marks et al., J. Mol. Biol. 222:581-597 (1991), for example.

Many warm-blooded animals, in particular mammals such as humans, rabbits, mice, rats, sheep, cows or pigs and ayes such as chickens and turkeys, may be used in order to obtain antibody-forming cells. However, rabbits and mice are generally preferred because of their ease in handling, well-defined genetic traits, and the fact that they may be readily sacrificed. Procedures for immunizing animals are well known in the art, and are described in Harlow et al., (*Antibodies: A Laboratory. Manual*, First Edition (1988) Cold Spring Harbor, N.Y.).

Once a suitable animal containing an antibody-producing cell has been identified or produced, spleen, lymph node or bone marrow tissue is typically removed, and a cell suspension of antibody-producing cells is prepared using techniques well known in the art. In most embodiments, this suspension is a single cell suspension, techniques for the preparation of which are well known in the art, e.g., Harlow et al., (Antibodies: A Laboratory Manual, First Edition (1988) Cold Spring Harbor, N.Y.).

Hybridomas are then produced by fusing the antibody-producing cells obtained from the animal so immunized and myeloma cells incapable of producing auto-antibodies. Then the hybridomas are cloned, and clones producing the monoclonal antibodies showing the specific affinity to the antigen used for immunizing the mammal are screened. In other embodiments, monoclonal antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-immunoglobulin column or protein A column.

A polyclonal antibody (antiserum) or monoclonal antibody can be produced by known methods. Namely, mammals, preferably, mice, rats, hamsters, guinea pigs, rabbits, cats, dogs, pigs, goats, horses, or cows, or more preferably, mice, rats, hamsters, guinea pigs, or rabbits are immunized, for example, with an antigen mentioned above with an adjuvant, if necessary. The polyclonal antibody can be obtained from the serum obtained from the animal so immunized.

In one aspect of any of the claimed methods, rabbit monoclonal antibodies are used to provide a phosphorylation specific antibody capable of specifically binding to phosphorylated yeast Ugp1 or PASK. Rabbit monoclonal antibodies provide the combined benefits of superior antigen recognition of the rabbit immune system with the specificity and consistency of a monoclonal antibody. Methods for creating and selecting rabbit antibodies are described in U.S. Pat. Nos. 5,675,063; 7,402,409; 7,429,487 & 7,575,896.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (Bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

In an alternative embodiment of any of the methods of the instant invention, peptide or RNA aptamer reagents, or non immunoglobulin based binding proteins such as Avimers can be substituted for one or more of the antibody reagents used. Such binding proteins can interact with proteins with specificity comparable to antibodies, and thus can substitute for antibody reagents in the determination of the level of phosphorylation of PASK or yeast Ugp1. Methods for selecting an appropriate peptide or RNA aptamer that is specific to the protein of interest are well known in the art (e.g. see Buerger, C. et al. et al. (2003) J. Biol. Chem. 278:37610-37621; Chen, C-H. B. et al. (2003) Proc. Natl. Acad. Sci. 100:9226-9231; and Buerger, C. and Groner, B. (2003) J. Cancer Res.: Clin. Oncol. 129(12):669-675. Epub 2003 Sep. 11; and the references cited therein).

A variety of methods are available to covalently label antibodies to enable direct detection or enzymatic amplification. Methods are selected based upon the nature of the member of the specific binding pair, the type of linkage desired, and the tolerance of the antibody to various conjugation chemistries. Biotin can be covalently coupled to antibodies by utilizing commercially available active derivatives. Examples include biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Several different N-hydroxysuccinimide esters of biotin are commercially available, with varying properties and spacer arm length (Pierce, Rockford, Ill.).

Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional cross-linking, and heterobifunctional crosslinking. Carboduimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available beterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The labeled primary antibody or secondary antibody, may be prepared by coupling to a reporter, which can be a radioactive isotope, enzyme, fluorogenic, chemiluminescent or electrochemical materials. Standard radioactive isotopic labeling procedures include the chloramine T, lactoperoxidase and Bolton-Hunter methods for example $^{125}$I and reductive methylation for $^3$H.

Enzymes suitable for use in this invention include, but are not limited to, horseradish peroxidase, alkaline phosphatase, (Berger, J., et al. (1988) Gene 66 1-10; Kain, S. R. (1997) Methods. Mol. Biol. 63 49-60), beta-galactosidase, (See, U.S. Pat. No. 5,070,012, and Bronstein, I., et al., (1989) J. Chemilum. Biolum. 4 99-111), glucose oxidase, luciferases, including firefly and renilla (U.S. Pat. Nos. 5,221,623; 5,683,888; 5,674,713; 5,650,289; 5,843,746), beta-lactamase (U.S. Pat. Nos. 5,741,657 and 5,955,604), urease, naturally fluorescent proteins (Tsien, R. Y. (1998) Annu. Rev. Biochem. 67 509-44) and lysozyme.

Enzyme labeling is facilitated by using dialdehyde, carboduimide coupling, homobifunctional crosslinkers and heterobifunctional crosslinkers as described above. The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled primary antibody can be detected by reacting the unlabeled antibody with a labeled secondary antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of any of the claimed methods biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one embodiment of any of the claimed methods the sample of cells is treated with a reagent in order to solubilize the PASK or yeast Ugp1 prior to determining its level of phosphorylation. In one aspect, solubilization is achieved via the addition of a protein-denaturing detergent, e.g. SDS. In another embodiment, solubilization is achieved via the addition of a chaotropic agent, e.g. urea, guanidinium hydrochloride. In another embodiment, solubilization is achieved via the addition of a commercially available protein solubilizing reagent termed PROTEOEXTRACT®. (Calbiochem, San Diego, Calif.).

VI. Exemplary Cell Lines

In one embodiment of any of the claimed methods the "sample" represents a sample of cells. In one aspect such samples of cells comprise cells grown in a tissue culture dish, plate or flask, e.g. a multi-well plate (e.g. 96-well). The cells may be grown for example in monolayer, suspension, or on beads. A number of suitable mammalian host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, screening and cloning of such cells are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. The methods of the instant invention can also be used in a compound screen to identify new PAS kinases, or to test the intracellular effects of known, or previously unknown, PAS kinase modulators, either in tissue or organ culture.

VII. High Throughput Screening Systems

In one embodiment, the methods of the instant invention can be used in a high-throughput screen (HTS) of compounds to identify PAS kinase inhibitors that have activity either in vitro or on whole cells. High throughput screening approaches are well known in the art and can be readily applied to identify screen for inhibitors using the claimed methods (see, e.g., Olsen et al., Methods. Mol. Biol. (2003) 230: 329-349; Turner, Trends Biotechnol. (2003) 21 (11): 474-478; Zhao et al., Curr. Opin. Biotechnol. (2002) 13 (2): 104-110; and Mastrobattista et al., Chem Biol. (2005) 12 (12): 1291-300).

Many high throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

In another embodiment, the methods of the instant invention can be used to compare potencies of PAS kinase inhibitor compounds by assaying two or more compounds over a range of concentrations under identical incubation conditions and comparing the relative potencies.

In any of the claimed methods, a control sample can mean i) a sample that was not incubated with a test compound or agent, ii) a zero time sample, iii) a zero time sample that was contacted with a test compound, iv) a sample that was contacted with a compound known to be capable of modulating PAS kinase activity, v) a sample incubated under conditions known to increase or decrease PAS kinase activity, vi) a sample lacking PAS kinase, or comprising a mutant of PASK with constitutive or no activity, vii) a sample lacking yeast Ugp1, or one or more reagents, such as for example, ATP or magnesium.

VIII. Kits

Also encompassed by the present invention are kits for detecting PAS kinase activity. In one embodiment, a kit according to the present invention comprises: (a) one or more antibody reagents, wherein the antibody reagent is specific to one or more phosphorylation sites PASK, and (b) instructions and/or promotional materials including details regarding using the antibody reagent to detect PAS Kinase activity. In some embodiments, kits featured herein further include an expression vector comprising DNA encoding PASK. In further embodiments the antibody reagent is specific to an AKT phosphorylation site on the PASK.

In another embodiment, a kit according to the present invention comprises: (a) one or more antibody reagents, wherein the antibody reagent is specific to one or more kinase phosphorylation sites on yeast Ugp1, and (b) instructions and/or promotional materials including details regarding using the antibody reagent to detect PAS Kinase activity. In some embodiments, kits featured herein further include an expression vector comprising DNA encoding yeast Ugp1.

All publications, patents and patent applications are herein expressly incorporated by reference in their entirety to the same extent as if each individual publication, patent or patent application was specifically and indicated individually to be incorporated by reference in its entirety. The following examples illustrate but are not intended in any way to limit the scope of the invention.

EXAMPLES

Example 1

Use of Phospho-Specific Ugp1 Antibody for Detection of PASK Activity

Introduction:

This assay has been developed to monitor Ugp1 phosphorylation by PASK in cell culture. In brief, cells are co-transfected with a human PASK expression vector and wild-type yeast Ugp1 expression vector. 12-72 hours post transfection cells are lysed, the cell lysate separated by SDS-PAGE and transferred to a nitrocellulose filter for Western blotting. The Western blots are then probed with both an Ugp1 antibody, which recognizes both the phosphorylated and unphosphorylated forms of Ugp1, and a phospho-specific Ugp1 rabbit antibody (generated by Epitomics). The results demonstrate the ability to monitor changes in PAS kinase activity within a living mammalian cell.

Methods:

Hek 293T cells were maintained and propagated in 10 cm dish in 10 ml of DMEM/10% FBS, split and re-seeded in 6 well plate ($10^6$ cells/well) in 2 ml of DMEM/10% FBS. Cells were transfected 18 hours post plating with 2 ug of PASK expression vector (pcDNA3.1) and 2 ug of wild-type yeast Ugp1 expression vector (pcDNA3.1) using Lipofectamine 2000 according to the manufacturers protocol (Invitrogen). 12 hours after transfection, the medium was aspirated and cells were lysed in a solution of hot (65° C.) Laemlli's sample buffer. Lysates were vortexed vigorously for at least 5 minutes and then boiled at 95° C. for 5 min. Lystates were then centrifuged to remove cellular debris and the supernatant was removed. The supernatant was separated on SDS-PAGE gel, followed by transfer to nitrocellulose membrane. The membrane was then blocked using a solution of 5% bovine serum albumin (BSA). Following blocking, the membrane was incubated with the antibody in a 5% BSA solution for 16 hours at 4° C. The membrane was then washed and incubated with a secondary antibody. After a final series of washings, the membrane was developed with a standard enhanced chemiluminescence system.

Results:

FIG. 1A) Lane 1 Shows the results obtained with an *S. cerevisiae* mutant strain lacking the two yeast PAS kinase orthologs, Psk1 and Psk2, which is known to have unphosphorylated Ugp1. Lane 5 shows the results obtained using an extract obtained from an *S. cerevisiae* mutant strain lacking the REG1 gene, this strain is known to have constitutively phosphorylated Ugp1. Note the non-specific band running immediately below the phospho-Ugp1 band in lane 5 indicated with the arrow. FIG. 1 B) Shows the results obtained with extracts from HEK293T human cultured cells that were transfected with human PASK and wild-type yeast Ugp1 (to promote phosphorylation) (lane 1), or with a Ugp1-S11A mutant to eliminate phosphorylation (lane 2), or with empty vector (lane 3). Note the non-specific band running just above the phospho-Ugp1 band in lane 1—indicated with the arrow.

Example 2

Determination of PAS Kinase Activity by Vivo $^{32}$P-Labeling

Introduction:

This protocol describes the procedure to determine PASK activity in the presence of PASK inhibitors by determining in vivo PASK phosphorylation. In brief, a cell line such as HEK293T expressing an epitope tagged PASK is incubated in low phosphate media to phosphate starve the cells for 30 minutes, followed by re-phosphorylation of cellular proteins in the presence of $^{32}$P-labeled phosphate. Cells are lysed and PASK is separated by immunoprecipitation from cell lysate with V5-epitope specific antibody. Samples are separated by SDS-PAGE and transferred on to nitrocellulose membrane by Western blotting. Fractions corresponding to PASK are assessed for $^{32}$P incorporation by autoradiography and normalized to the total PASK amount in immunoprecipitates determined by probing with a V5 specific antibody.

Method:

HEK293T cells were maintained and propagated in 10 cm dishes in 10 ml of DMEM/10% FBS, split and re-seeded in 6 well plate ($10^6$ cells/well) in 2 ml of DMEM/10% FBS. Cells were transfected 18 hours post plating with 1 ug of V5-tagged PASK expressing vector (pcDNA3.1-V5-PASK) and lipofectamine 2000 according to the manufacturers protocol (Invitrogen). Twelve hours after transfection, the medium was aspirated and replaced with 2 ml of DMEM/10% FBS supplemented with DMSO or the PASK inhibitors to be tested in the desired concentrations. Cells were incubated for 2 hours at 37 C and then washed two times with 2 ml of phosphate free DMEM, followed by incubation with 0.1 mCi ortho-$^{32}$P phosphate/well in the presence of DMSO or compounds. Following a 4 hour incubation with $^{32}$P the cells were washed with phosphate free DMEM to remove unbound radiation, lysed using 0.3 ml lysis buffer (20 mM $Na_2HPO_4$, 0.5% Triton, 0.1% SDS, 0.02% azide, containing protease and phosphatase inhibitors—1 mM NaF, 1 mM glycerphosphate, 1 mM $Na_3VO_4$) and immunoprecipitated with VSAB conjugated beads (Sigma). Bound Immunocomplexes were washed with buffer (20 mM $Na_2HPO_4$, 0.5% Triton X-100, 0.1% SDS, 0.02% $NaN_3$) containing high salt (1M NaCl and 0.1% BSA) followed by low salt (150 mM NaCl). Immunoprecipitated PASK was released from the immunocomplexes by boiling with SDS-PAGE sample buffer, and separated by SDS-PAGE and transferred on nitrocellulose membrane. Autoradiography was applied to determine the fraction of $^{32}$P-labelled PASK and normalized to total PASK detected by Western blot.

Figure 2A:
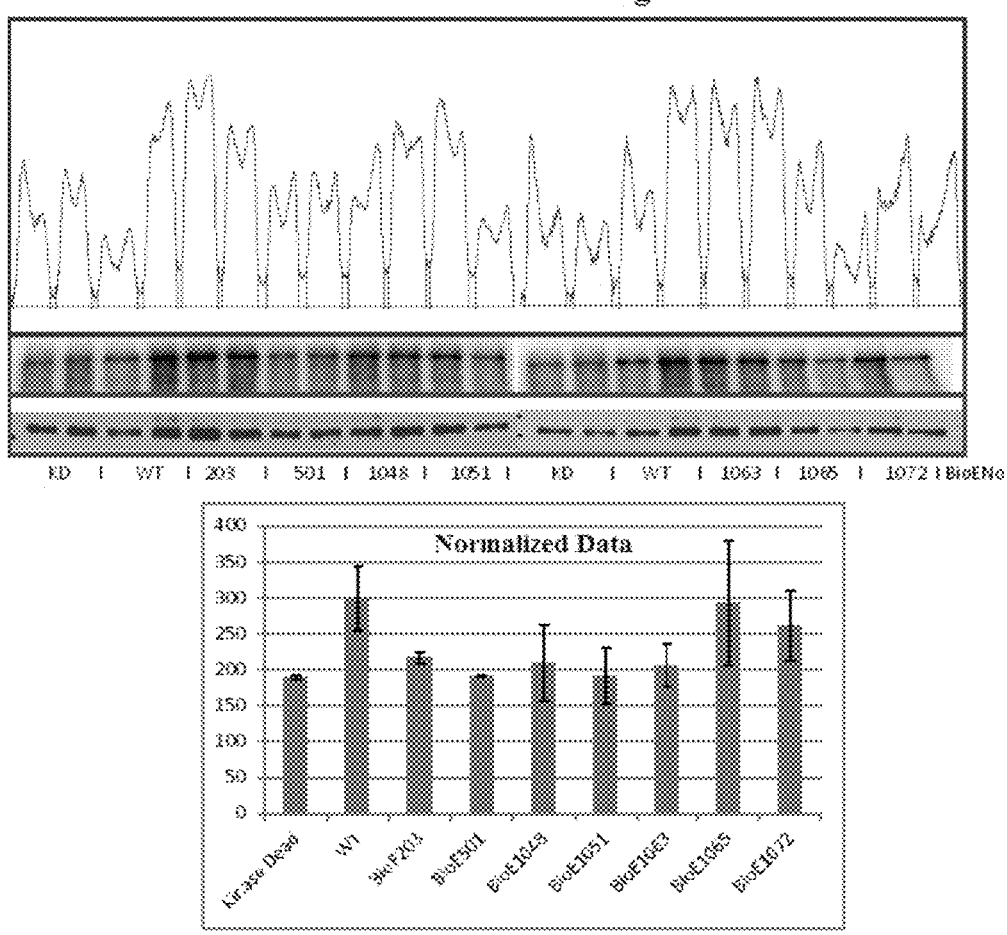
FIG. 2A (Upper panel) Shows $^{32}P$ incorporation into immunoprecipitated fractions corresponding to PASK obtained after whole cell $^{32}P$ labeling. The lower panel shows that after radioactive incorporation has been normalized to take into account the total amount of PASK in immunoprecipitates determined by probing with a V5 epitope specific antibody, that the treatment of the cells expressing PASK with putative inhibitors leads to a reproducible and significant reduction of PASK phosphorylation.
Figure 2B:
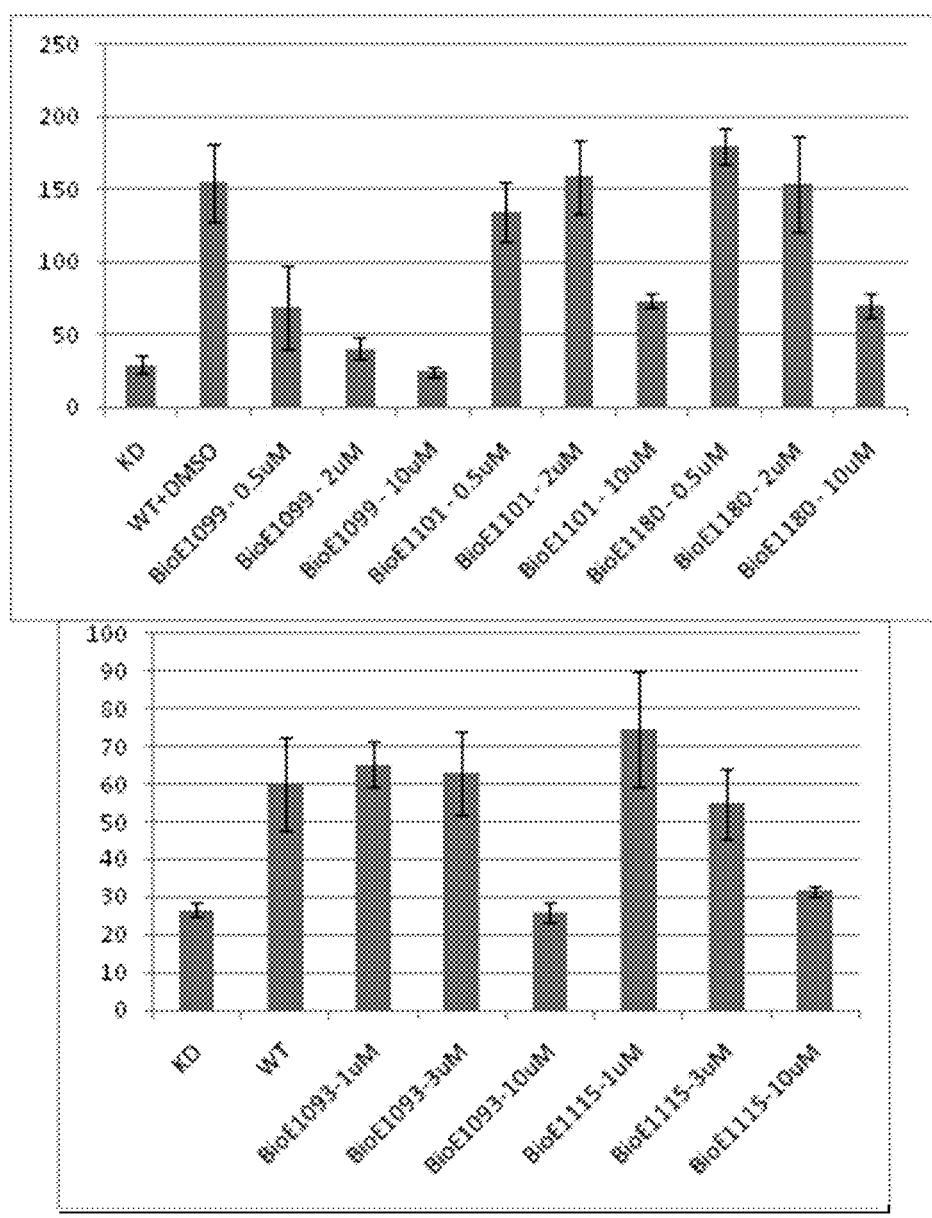
FIG. 2B shows that this assay is able to generate reproducible dose response data in a high throughput screening format to detect PASK inhibitors.

Results:

As shown in FIG. 2A, (upper panel) metabolic labeling with 32P resulted in variable incorporation into the immunoprecipated protein. However after normalization, (lower panel) treatment of the cells expressing PASK with putative inhibitors leads to a reproducible and significant reduction of PASK phosphorylation. A PASK mutant with no activity (comprising a K1028→R mutation) (Kinase Dead or "KD" in FIG. 2) shows a significant reduction of $^{32}$P incorporation relative to wild-type PASK (WT). These data serve as controls. Compounds are then tested for effect on PASK $^{32}$P incorporation as shown, with some showing a decrease of similar magnitude to the KD PASK and others showing little or no decrease. FIG. 2B shows that the assay generated reproducible and consistent data to enable the generation of meaningful dose dependency data.

Example 3

Use of Phospho-AKT Substrate Antibody to Determine PAS Kinase Activity

Introduction:

The assay relies on the ability of PASK to autophoshorylate in vivo at sequence(s) recognized by phosphospecific antibody (110B7E, Cell Signaling), which recognizes the Akt phosphorylation motif (SEQ. ID. Nos. 32 and 33). In brief, HEK293T cells were transfected with an expression vector (pcDNA 3.1-PASK) expressing either a V5-tagged wild-type human PASK or an inactive (kinase dead or KD) version (comprising a K1028→R mutation) of PASK. Expression vectors contained PASK cloned in frame with a C-terminal V5 tag such that the PASK protein is expressed as a fusion protein with the V5 epitope at its C-terminus. Transfected cells were then treated with putative inhibitors of PASK. Twenty-four hours post treatment cells were lysed and PASK was separated from cellular proteins by immunoprecipitation with V5-conjugated beads (Sigma). Immunocomplexes were washed, and the samples then released from immunocomplexes, separated on the SDS-PAGE gel, and transferred on nitrocellulose membrane, as described above. Fractions of PASK phosphorylated at the sites recognized by the phospho-AKT specific antibody were determined, and the results normalized to the total PASK level present in the same immunoprecipitates.

Method:

HEK293T cells were maintained and propagated in 10 cm dishes in 10 ml of DMEM/10% FBS, split and re-seeded in 6 well plates at a density of $10^6$ cells/well in 2 ml of DMEM/10% FBS. Cells were transfected 18 hours post plating with 1 ug of the expression vector expressing either wild-type or the kinase dead mutant of human PASK using lipofectamine 2000 according to the manufacturer's protocol (Invitrogen). Cells expressing PASK were treated either with DMSO or PASK inhibitors and maintained at 37 C. Twenty-four hours post transfection, medium was aspirated and cells were lysed in 0.5 ml of lysis buffer (20 mM Na2HPO4, 0.5% Triton, 0.1% SDS, 0.02% azide, also containing proteases, and phosphatases Inhibitors—1 mM NaF, 1 mM glycerphosphate, 1 mM $Na_3VO_4$) and immunoprecipitated with V5AB conjugated beads (Sigma). Immunocomplexes were washed with buffer (20 mM $Na_2HPO_4$, 0.5% Triton X-100, 0.1% SDS, 0.02% $NaN_3$) containing high salt (1M NaCl and 0.1% BSA) followed by low salt (150 mM NaCl). Immunoprecipitated PASK was released from immunocomplexes and separated by SDS-PAGE and transferred on nitrocellulose membrane (Western blot). Blots were probed subsequently with an antibody specific for AKT phosphorylation sites on PASK (SEQ. ID Nos 28 to 30) and V5 epitope specific antibody. Intensities of the bands were quantitated. The band intensity in the phospho-AKT substrate immunoblot was divided by the intensity of the V5 immunoblot and this normalized value was used as a measure of stoichiometry of phosphorylation. Inhibition curve fitting and $IC_{50}$ values were determined with Prism software (GraphPad).

Results:

Here an antibody specific for AKT phosphorylation motifs is utilized to monitor in vivo autophosphorylation ability (activity) of PASK in the presence of its putative inhibitors.

Figure 3:
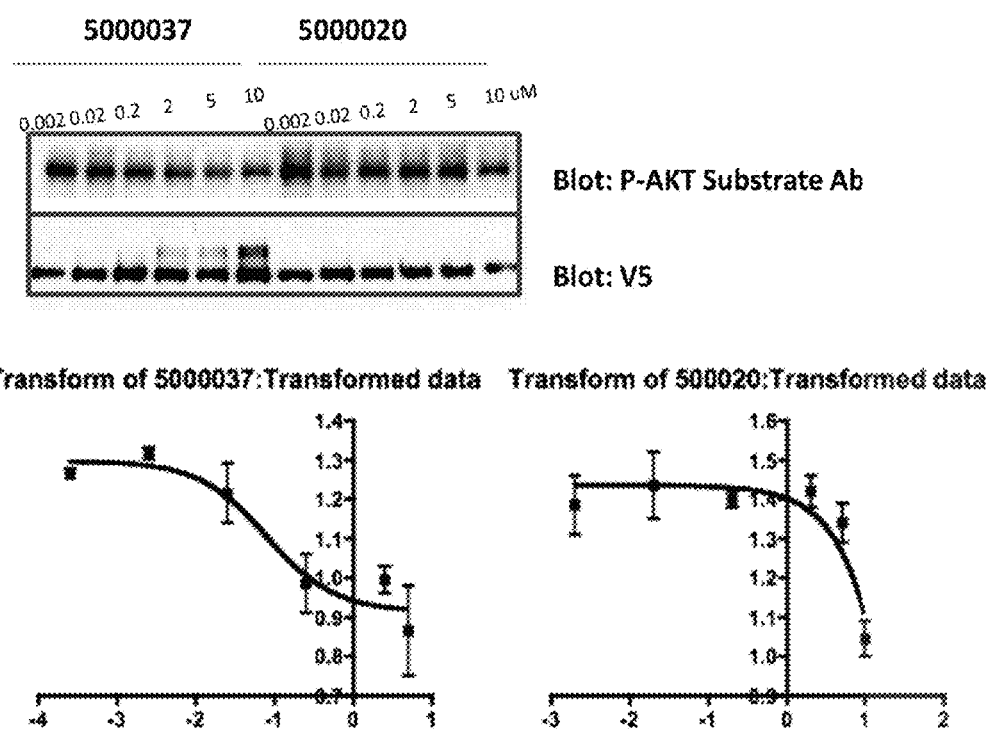
FIG. 3 Shows an exemplary western blot for two small molecule PASK inhibitors and the associated transformed data plots which demonstrate that assay provides reliable and reproducible dose response data sets.

FIG. 3 shows an exemplary western blot for two small molecule PASK inhibitors and the associated transformed data plots which demonstrate that assay provides reliable and reproducible dose response data sets.

Figure 4:
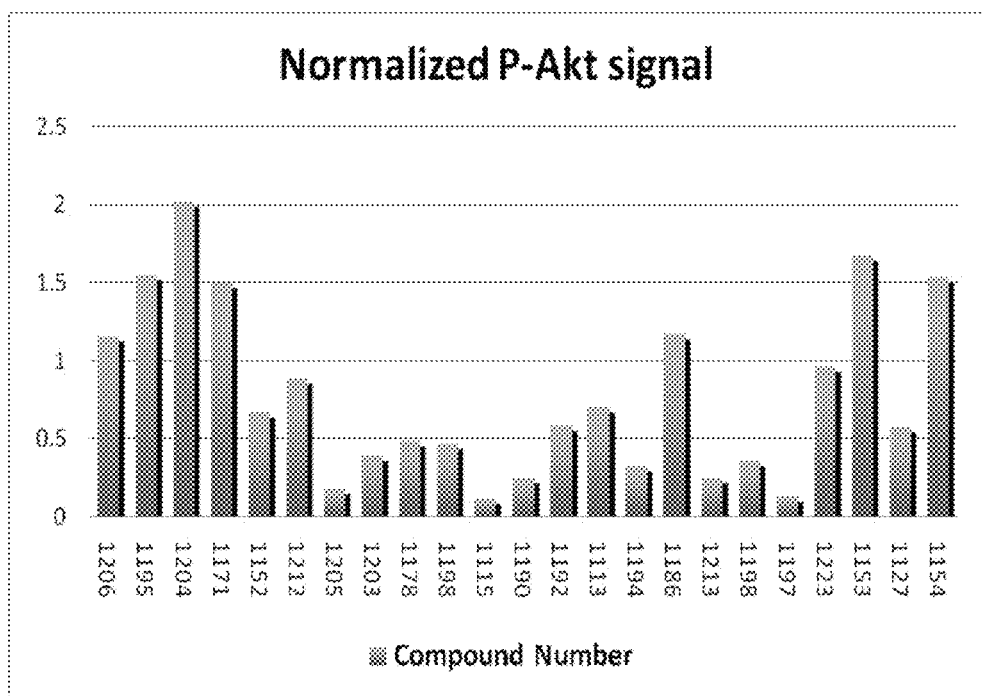
FIG. 4 Shows the results of screening a panel of potential PASK inhibitors by measuring the PASK phosphorylation level via the use of an antibody specific to the AKT phosphorylation motif.

FIG. 4 demonstrates that the wild-type PASK but not the kinase-dead mutant of PASK, is phosphorylated in vivo on a sequence recognized by a phosho-AKT specific substrate antibody, and that this assay methodology is sensitive enough to detect the pharmacological inhibition of PASK by small molecule inhibitors.

Figure 5:
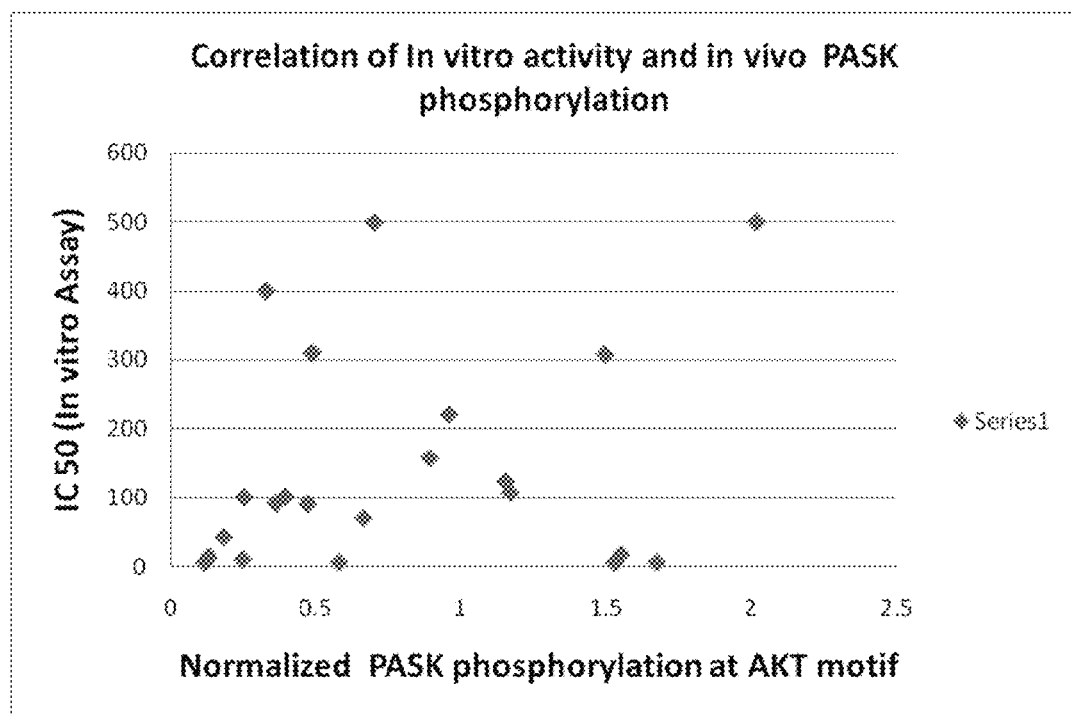
FIG. 5 Shows the correlation of apparent potencies for a series of potential PASK inhibitors determined either via an in vitro kinase assay, or determined via measuring the phosphorylation state of PASK in situ using a phosphospecific antibody specific for the AKT phosphorylation motif.

In FIG. 5, the results obtained with the phospho-AKT specific antibody were compared directly with an in vitro kinase assay for PAS kinase. In the in vitro assay, PASK activity was determined by the addition of recombinant PASK (UniProt #Q96RG2; human recombinant N-terminal GST tagged construct, residues 879-1323) from insect cells, final concentration 5 nM) to freshly prepared Base Reaction Buffer containing 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO and Myelin Basic Protein (20 µM final). Test compounds in DMSO were then added to the mixture, followed by delivery of $^{33}$P-ATP (specific activity 0.01 µCi/µl final) to initiate the reaction. The kinase reaction was incubated for 120 min at room temperature. The entire reaction mixture was then transferred onto a P81 Phosphocellulose paper (Whatman #3698-915) and washed extensively with 0.1% phosphoric acid and once in methanol prior to drying and scintillation counting.

In FIG. 5, the X-axis is the normalized amount of phosphorylated PASK, as determined via the use of the AKT phosphospecific antibody. On this scale "one" represents no inhibition and lower numbers indicates more inhibition. The Y-axis shows the IC50 of the same compounds using the in vitro biochemical assay described above. The data in FIG. 5 shows that although there are some outliers in the data set, there is an overall correlation in IC50 value and degree of inhibition of intracellular PASK phosphorylation, as determined using an AKT phosphospecific antibody.

Thus this data demonstrates that measuring intracellular PASK activity via this approach provides a reliable and sensitive method which enables PASK activity in vivo to be determined under desired conditions, and in particular provides a sensitive and robust assay methodology for drug discovery.

Example 4

Use of Phospho-AKT Substrate Antibody to Determine PAS Kinase Activity in an ELISA Assay Introduction: As described previously, this assay relies on the ability of PASK to autophoshorylate in vivo at sequence(s) recognized by phosphospecific antibody (110B7E, Cell Signaling), which recognizes the Akt phosphorylation motif (SEQ. ID. Nos. 32 and 33). PASK inhibitors reduce the degree of autophosphorylation of PASK which as a result, displays reduced reactivity with the 110B7E antibody. In order to detect the phosphorylated fraction of PASK in each sample, we developed Enzyme-linked immunosorbent assay (ELISA). Here, an unknown amount of PASK from each inhibitor treated cell sample is affixed to FLAG antibody coated surface, and then P-AKT substrate specific antibody is applied over the surface so it can bind to PASK antigen. This antibody is than detected by secondary rabbit antibody linked to HRP enzyme. Luminescence is detected in the microplate reader.

Method: HEK293T cells were seeded in 10 cm plates at a density of 6×10$^6$ cells/well in 10 ml of DMEM/10% FBS. Cells were transfected 5 hours post plating with Bug of the pcDNA 3.1-FLAG-PASK vectors expressing either wild-type or the kinase dead mutant of human PASK. Transfection was performed using lipofectamine 2000 according to the manufacturer's protocol (Invitrogen). Eighteen hours later the cells were split and re-seeded into 96 well cell culture plates at a density of 3×10$^4$ cells/well in 200 ul of DMEM/1% FBS. Cells expressing PASK were treated either with DMSO or PASK inhibitors and maintained at 37 C. Sixteen hours post treatment, medium was aspirated and cells were lysed in 0.2 ml of lysis buffer (20 mM Na2HPO4, 0.5% Triton, 0.1% SDS, 0.02% azide, also containing proteases, and phosphatases Inhibitors—1 mM NaF, 1 mM glycerphosphate, 1 mM Na$_3$VO$_4$). The lysates were then applied to MaxiSorp™ 96 well plate (Nunc), previously coated for 24 hours with ANTI-FLAG (sigma, M2) capture antibody and subsequently blocked with 3% BSA (in 1×PBS) for 2 hours at room temperature. Lysates were incubated for 1.5 hours in 4° C. with capture antibody and subsequently plates were washed with wash buffers (20 mM Na$_2$HPO$_4$, 0.5% Triton X-100, 0.1% SDS, 0.02% NaN$_3$) containing high salt (1M NaCl and 0.1% BSA) followed by low salt (150 mM NaCl). Next, plates were incubated for 2 h either with 1) phospho-Akt substrate antibody (Phospho-AKT Substrate rabbit mAb, Cell Signaling 110B7E, 1:1000 dilution) or 2) hPASK specific antibody (rabbit U2501, Rutter lab, 1:1000 dilution) followed by high and low salt buffer washes (as described above). Subsequently plates were incubated with HRP-conjugated secondary antibody (rabbit 1:10000 dilution) for 1 hr and then washed with respectively high, low salt buffers (as described above) and 1×PBS.

Finally, luminescence signal either P-AKT substrate or PASK (U2501) antibody dependent was detected with LumiGLO® chemiluminescent substrate system (KPL) according to manufacturer's protocol and microplate reader. P-AKT substrate dependent signal was normalized to the total PASK in each sample, quantitated with U2501 antibody. Inhibition curve and IC$_{50}$s were determined with Prism software (GraphPad).

Figure 6:
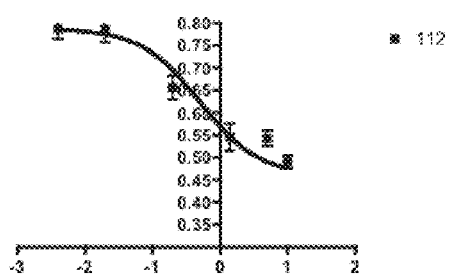
FIG. 6 Shows the results of screening exemplary potential PASK inhibitors using an ELISA assay to determine the phosphorylation status of PASK.
Figure 6:
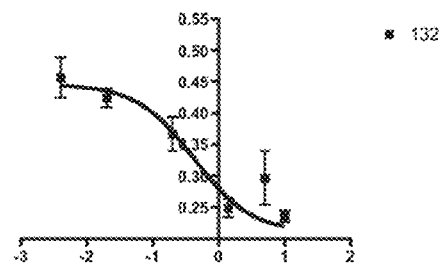
Figure 6:
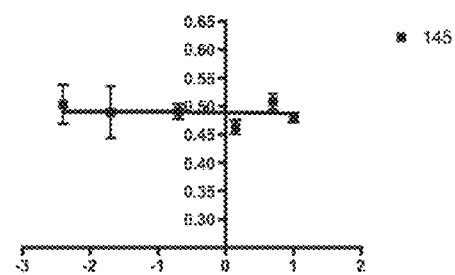
Figure 6:
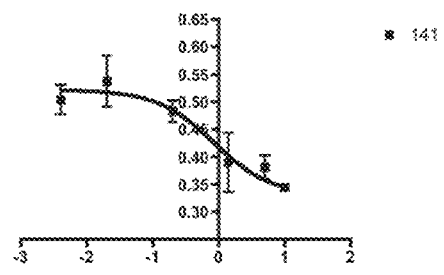

Results: The results from theses screens, shown in FIG. 6 demonstrate that the Phospho-AKT substrate antibody can be used to create a quantitative ELISA assay of PASK autophosphorylation status that can be used to detect and measure the ability of putative PASK modulators to impact the level of PASK autophosphorylation and thereby their ability to modulate the activity of PAS kinase.

The invention claimed is:

1. A method for determining the PAS kinase inhibiting properties of a compound comprising;
   a) contacting a sample comprising PAS kinase activity with the compound and measuring the level of phosphorylation of the PAS kinase in the sample; and
   b) comparing the PAS kinase phosphorylation levels of the sample contacted with the compound with the phosphorylation levels of PAS kinase in a control sample,
   wherein the level of PAS kinase phosphorylation correlates with the level of intracellular PAS kinase activity.

2. A method for identifying an agent that modulates the intracellular activity of PAS kinase comprising;
   a) providing a test sample comprising PAS kinase activity,
   b) determining the change in phosphorylation of the PAS kinase in the test sample by contacting the sample with a test agent and comparing the PAS kinase phosphorylation level with the phosphorylation level of a PAS kinase in a control sample, and
   c) determining whether the test agent is an agent that modulates the intracellular activity of PAS kinase based on a change in phosphorylation state of PAS kinase in the test sample compared to the control sample, wherein the level of PAS kinase phosphorylation correlates with the level of intracellular PAS kinase activity.

3. The method of either of claim 1 or 2, wherein the sample comprises purified PAS kinase.

4. The method of either of claim 1 or 2, wherein the sample comprises mammalian cells which express PAS kinase.

5. The method of claim 4, wherein the mammalian cells are transfected, or transformed with a nucleic acid encoding human PAS kinase.

6. The method of claim 5, wherein the PAS kinase is epitope tagged.

7. The method of claim 4, wherein the level of PAS kinase phosphorylation is determined via measuring $^{32}P$ incorporation into PAS kinase.

8. The method of claim 4, wherein the level of phosphorylation of PAS kinase is determined using an antibody reagent which is specific to one or more phosphorylation sites on PAS kinase.

9. The method of claim 4, wherein the level of phosphorylation of PAS kinase is determined by electrophoretic separation of the proteins in the sample and immunoblot analysis using an antibody reagent specific to PAS kinase.

10. The method of claim 4, wherein the level of phosphorylation of PAS kinase is determined using a first antibody reagent which is specific to PAS kinase and a second antibody reagent which is specific to one or more phosphorylation sites on PAS kinase.

11. The method of claim 4, wherein the level of phosphorylation of PAS kinase is determined using an ELISA assay.

12. The method of claim 8, wherein the antibody reagent which is specific to one or more phosphorylation sites on PAS kinase is specific for phosphoserine.

13. The method of claim 8, wherein the antibody reagent which is specific to one or more phosphorylation sites on PAS kinase is specific for phosphothreonine.

14. The method of claim 8, wherein the antibody reagent which is specific to one or more phosphorylation sites on PAS kinase is specific for an AKT phosphorylation site.

15. The method of claim 14, wherein the AKT phosphorylation site is selected from the group consisting of sequence RXXS (SEQ. ID. No. 28), RXXT (SEQ. ID. No. 29), RRXS (SEQ. ID. No. 30), RRXT (SEQ. ID. No. 31), RXRXXS (SEQ. ID. No. 32), and RXRXXT (SEQ. ID. No 33), where "X" in any of SEQ. ID. Nos 28 to 33 can be any amino acid.

16. The method of claim 15, wherein the level of PAS kinase phosphorylation is determined at position T307 of the PAS kinase.

* * * * *